(12) United States Patent
Batchelor et al.

(10) Patent No.: US 11,298,801 B2
(45) Date of Patent: *Apr. 12, 2022

(54) BIAS DEVICE FOR BIASING A GRIPPING DEVICE INCLUDING A CENTRAL BODY AND SHUTTLES ON THE WORKING ARMS

(71) Applicant: GYRUS ACMI, INC., Southborough, MA (US)

(72) Inventors: Kester J. Batchelor, Mound, MN (US); Riyad Moe, Madison, WI (US)

(73) Assignee: Gyrus Acmi, Inc., Westborough, MA (US)

( * ) Notice: Subject to any disclaimer, the term of this patent is extended or adjusted under 35 U.S.C. 154(b) by 820 days.

This patent is subject to a terminal disclaimer.

(21) Appl. No.: 15/801,583

(22) Filed: Nov. 2, 2017

(65) Prior Publication Data

US 2019/0126442 A1 May 2, 2019

Related U.S. Application Data

(63) Continuation-in-part of application No. 15/801,379, filed on Nov. 2, 2017, and a continuation-in-part of application No. 15/801,533, filed on Nov. 2, 2017.

(51) Int. Cl.
*A61B 17/28* (2006.01)
*A61B 18/14* (2006.01)
(Continued)

(52) U.S. Cl.
CPC .............. *B25B 7/18* (2013.01); *A61B 17/282* (2013.01); *A61B 18/1442* (2013.01);
(Continued)

(58) Field of Classification Search
CPC ...... A61B 17/30; A61B 2017/301–308; A61B 18/085; A61B 18/1442–1447;
(Continued)

(56) References Cited

U.S. PATENT DOCUMENTS

| 1,198,958 | A | 9/1916 | Risely |
| 2,042,985 | A | 6/1936 | Gardella |

(Continued)

FOREIGN PATENT DOCUMENTS

| EP | 0392548 A1 | 10/1994 |
| EP | 1530952 A1 | 5/2005 |

(Continued)

OTHER PUBLICATIONS

Potentially related U.S. Appl. No. 14/589,482, filed Jan. 5, 2015 published as 2015/0148798 on May 28, 2015.

(Continued)

*Primary Examiner* — Majid Jamialahmadi
(74) *Attorney, Agent, or Firm* — Schwegman Lundberg & Woessner, P.A.

(57) ABSTRACT

A device comprising: (a) a first working arm; (b) a body; (c) a shuttle, and (d) a bias device; wherein the bias device biases the first working arm relative to the body when the shuttle is in a first position, and wherein the bias device is free of biasing the first working arm relative to the body when the shuttle is in a second position.

21 Claims, 8 Drawing Sheets

(51) Int. Cl.
*B25B 7/18* (2006.01)
*B25B 7/08* (2006.01)

(52) U.S. Cl.
CPC ............ *A61B 18/1445* (2013.01); *B25B 7/08* (2013.01); *A61B 17/2841* (2013.01); *A61B 18/1447* (2013.01); *A61B 2018/1462* (2013.01)

(58) Field of Classification Search
CPC .................. A61B 2018/145–1462; A61B 2018/00589–00595; A61B 2018/00607; A61B 10/06; A61B 17/282; A61B 17/2841; A61B 18/1445; A61B 18/1447; A61B 2018/1466; B25B 9/00–04
See application file for complete search history.

(56) References Cited

U.S. PATENT DOCUMENTS

| | | | |
|---|---|---|---|
| 2,214,984 A | 9/1940 | Bachmann | |
| 2,381,084 A | 8/1945 | Slad | |
| 2,575,652 A | 11/1951 | Bovee | |
| 2,894,424 A | 7/1959 | Vaughan | |
| 3,399,583 A | 9/1968 | Hall | |
| 3,417,752 A | 12/1968 | Butler | |
| 3,465,621 A | 9/1969 | Ladd | |
| 3,576,072 A | 4/1971 | Foster | |
| 3,643,663 A | 2/1972 | Sutter | |
| 3,685,518 A | 8/1972 | Beuerle et al. | |
| 3,699,632 A | 10/1972 | Anhalt | |
| 3,818,784 A | 6/1974 | McClure | |
| 3,906,957 A | 9/1975 | Weston | |
| 3,913,586 A | 10/1975 | Baumgarten | |
| 4,023,450 A | 5/1977 | Ygfors | |
| 4,041,952 A | 8/1977 | Morrison, Jr. et al. | |
| 4,154,226 A | 5/1979 | Hennig et al. | |
| 4,171,700 A | 10/1979 | Farin | |
| 4,202,337 A | 5/1980 | Hren et al. | |
| 4,318,313 A | 3/1982 | Tartaglia | |
| 4,375,218 A | 3/1983 | DiGeronimo | |
| 4,387,610 A | 6/1983 | Sergeant | |
| 4,407,069 A | 10/1983 | Conners | |
| 4,418,692 A | 12/1983 | Guay | |
| 4,443,935 A | 4/1984 | Zamba et al. | |
| 4,452,106 A * | 6/1984 | Tartaglia | A61B 17/2812 |
| | | | 294/902 |
| 4,462,404 A | 7/1984 | Schwarz et al. | |
| 4,463,759 A | 7/1984 | Garito et al. | |
| 4,492,231 A | 1/1985 | Auth | |
| 4,492,832 A | 1/1985 | Taylor | |
| 4,494,543 A | 1/1985 | Hart | |
| 4,504,707 A | 3/1985 | Ochiai | |
| 4,524,648 A | 6/1985 | Chung | |
| 4,552,143 A | 11/1985 | Lottick | |
| 4,655,215 A | 4/1987 | Pike | |
| 4,669,470 A | 6/1987 | Brandfield | |
| 4,686,980 A | 8/1987 | Williams et al. | |
| 4,713,885 A | 12/1987 | Keklak et al. | |
| 4,757,612 A | 7/1988 | Peyrot | |
| 4,784,136 A | 11/1988 | Klein | |
| 4,839,947 A | 6/1989 | Cohen et al. | |
| 4,860,745 A | 8/1989 | Farin et al. | |
| 4,896,661 A | 1/1990 | Bogert et al. | |
| 4,935,027 A | 6/1990 | Yoon | |
| 5,021,616 A | 6/1991 | Hardt | |
| 5,035,695 A | 7/1991 | Weber, Jr. et al. | |
| 5,071,426 A | 12/1991 | Dolgin et al. | |
| 5,104,397 A | 4/1992 | Vasconcelos et al. | |
| 5,108,392 A | 4/1992 | Spingler | |
| 5,147,378 A | 9/1992 | Markham | |
| 5,176,702 A | 1/1993 | Bales et al. | |
| 5,190,541 A | 3/1993 | Abele et al. | |
| 5,196,009 A | 3/1993 | Kirwan, Jr. | |
| 5,207,691 A | 5/1993 | Nardella | |
| 5,207,696 A | 5/1993 | Matwijcow | |
| 5,208,983 A | 5/1993 | Masse | |
| 5,226,904 A | 7/1993 | Gentelia et al. | |
| 5,250,056 A | 10/1993 | Hasson | |
| 5,281,216 A | 1/1994 | Klicek | |
| 5,290,286 A | 3/1994 | Parins | |
| 5,293,878 A | 3/1994 | Bales et al. | |
| 5,318,589 A | 6/1994 | Lichtman | |
| 5,342,359 A | 8/1994 | Rydell | |
| 5,370,659 A | 12/1994 | Sakashita | |
| 5,403,312 A | 4/1995 | Yates et al. | |
| 5,413,575 A | 5/1995 | Haenggi | |
| 5,423,814 A | 6/1995 | Zhu et al. | |
| 5,425,743 A | 6/1995 | Nicholas | |
| 5,440,813 A | 8/1995 | Roskam | |
| 5,441,498 A | 8/1995 | Perkins | |
| 5,443,463 A | 8/1995 | Stern et al. | |
| 5,456,695 A | 10/1995 | Dellamagne | |
| 5,458,598 A | 10/1995 | Fienberg et al. | |
| 5,472,442 A | 12/1995 | Klicek | |
| 5,483,952 A | 1/1996 | Aranyi | |
| 5,484,435 A | 1/1996 | Fleenor et al. | |
| 5,499,998 A | 3/1996 | Meade | |
| 5,531,744 A | 7/1996 | Nardella et al. | |
| 5,540,685 A | 7/1996 | Parins et al. | |
| 5,562,503 A | 10/1996 | Ellman et al. | |
| 5,573,424 A | 11/1996 | Poppe | |
| 5,619,892 A | 4/1997 | Eggert | |
| 5,626,577 A | 5/1997 | Harris | |
| 5,658,281 A | 8/1997 | Heard | |
| D386,054 S | 11/1997 | Litton | |
| 5,702,390 A | 12/1997 | Austin et al. | |
| 5,709,680 A | 1/1998 | Yates et al. | |
| 5,735,849 A | 4/1998 | Baden et al. | |
| 5,779,701 A | 7/1998 | McBrayer et al. | |
| 5,810,805 A | 9/1998 | Sutcu et al. | |
| 5,827,281 A | 10/1998 | Levin | |
| 5,884,954 A | 3/1999 | Trozera | |
| 5,891,140 A | 4/1999 | Ginn et al. | |
| 5,902,301 A | 5/1999 | Olig | |
| 5,922,001 A | 7/1999 | Yoon | |
| 5,951,545 A | 9/1999 | Schilling et al. | |
| 6,024,741 A | 2/2000 | Williamson, IV et al. | |
| 6,030,384 A | 2/2000 | Nezhat | |
| 6,039,734 A | 3/2000 | Goble | |
| 6,050,996 A | 4/2000 | Schmaltz et al. | |
| 6,053,908 A | 4/2000 | Crainich et al. | |
| 6,074,386 A | 6/2000 | Goble et al. | |
| 6,102,909 A | 8/2000 | Chen et al. | |
| 6,110,171 A * | 8/2000 | Rydell | A61B 18/1442 |
| | | | 606/48 |
| 6,113,596 A | 9/2000 | Hooven et al. | |
| 6,117,158 A | 9/2000 | Measamer et al. | |
| 6,117,169 A | 9/2000 | Moe | |
| 6,152,923 A | 11/2000 | Ryan | |
| 6,190,386 B1 | 2/2001 | Rydell | |
| 6,270,497 B1 | 8/2001 | Sekino et al. | |
| 6,273,887 B1 | 8/2001 | Yamauchi et al. | |
| 6,325,795 B1 | 12/2001 | Lindemann et al. | |
| 6,355,032 B1 | 3/2002 | Hovda et al. | |
| 6,358,268 B1 | 3/2002 | Hunt et al. | |
| 6,402,747 B1 | 6/2002 | Lindemann et al. | |
| 6,428,538 B1 | 8/2002 | Blewett et al. | |
| 6,458,128 B1 | 10/2002 | Schulze | |
| 6,464,704 B2 | 10/2002 | Schmaltz et al. | |
| 6,486,419 B2 | 11/2002 | Horiguchi et al. | |
| 6,494,886 B1 | 12/2002 | Wilk et al. | |
| 6,514,252 B2 | 2/2003 | Nezhat et al. | |
| 6,551,313 B1 | 4/2003 | Levin | |
| 6,585,735 B1 | 7/2003 | Frazier et al. | |
| 6,619,038 B2 | 9/2003 | Takada et al. | |
| 6,623,499 B1 | 9/2003 | Andreini et al. | |
| 6,641,595 B1 | 11/2003 | Moran et al. | |
| 6,652,514 B2 | 11/2003 | Ellman et al. | |
| 6,679,882 B1 | 1/2004 | Kornerup | |
| 6,695,840 B2 | 2/2004 | Schulze | |
| 6,726,686 B2 | 4/2004 | Buysse et al. | |
| 6,749,610 B2 | 6/2004 | Kirwan, Jr. et al. | |
| 6,752,767 B2 | 6/2004 | Turovskiy et al. | |
| 6,773,434 B2 | 8/2004 | Ciarrocca | |
| 6,808,525 B2 | 10/2004 | Latterell et al. | |

(56) References Cited

U.S. PATENT DOCUMENTS

| | | |
|---|---|---|
| 6,827,717 B2 | 12/2004 | Brommersma et al. |
| 6,860,882 B2 | 3/2005 | Battles et al. |
| 6,926,716 B2 | 8/2005 | Baker et al. |
| 6,942,662 B2 | 9/2005 | Goble et al. |
| 7,083,613 B2 | 8/2006 | Treat |
| 7,094,231 B1 | 8/2006 | Ellman et al. |
| 7,108,694 B2 | 9/2006 | Miura et al. |
| 7,112,199 B2 | 9/2006 | Cosmescu |
| 7,147,637 B2 | 12/2006 | Goble |
| 7,147,638 B2 | 12/2006 | Goble |
| 7,150,749 B2 | 12/2006 | Dycus et al. |
| 7,156,846 B2 | 1/2007 | Dycus et al. |
| 7,232,440 B2 | 6/2007 | Dumbauld et al. |
| 7,244,257 B2 | 7/2007 | Podhajsky et al. |
| 7,252,667 B2 | 8/2007 | Moses et al. |
| 7,344,536 B1 | 3/2008 | Lunsford et al. |
| 7,367,976 B2 | 5/2008 | Lawes et al. |
| 7,377,902 B2 | 5/2008 | Burbank |
| 7,481,810 B2 | 1/2009 | Dumbauld et al. |
| 7,503,917 B2 | 3/2009 | Sartor et al. |
| 7,604,635 B2 | 10/2009 | McClurken et al. |
| 7,625,391 B2 | 12/2009 | Kebel et al. |
| 7,674,261 B2 | 3/2010 | Garito et al. |
| 7,686,827 B2 | 3/2010 | Hushka |
| 7,722,607 B2 | 5/2010 | Dumbauld et al. |
| 7,753,909 B2 | 7/2010 | Chapman et al. |
| 7,758,577 B2 | 7/2010 | Nobis et al. |
| 7,789,878 B2 | 9/2010 | Dumbauld et al. |
| 7,879,035 B2 | 2/2011 | Garrison et al. |
| 7,896,875 B2 | 3/2011 | Heim et al. |
| 7,909,820 B2 | 3/2011 | Lipson et al. |
| 7,922,718 B2 | 4/2011 | Moses et al. |
| 7,931,649 B2 | 4/2011 | Couture et al. |
| 7,931,668 B2 | 4/2011 | Sloat |
| 7,938,469 B2 | 5/2011 | Ait-Mani |
| 7,942,872 B2 | 5/2011 | Ein-Gal |
| 7,955,331 B2 | 6/2011 | Truckai et al. |
| 7,998,140 B2 | 8/2011 | McClurken et al. |
| 8,062,292 B1 | 11/2011 | Slater |
| 8,100,894 B2 | 1/2012 | Mucko et al. |
| 8,162,940 B2 | 4/2012 | Johnson et al. |
| 8,216,231 B2 | 7/2012 | Behl et al. |
| 8,226,649 B2 | 7/2012 | Falkenstein et al. |
| 8,246,094 B2 | 8/2012 | Long et al. |
| 8,251,989 B1 | 8/2012 | Newton et al. |
| 8,262,655 B2 | 9/2012 | Ghabrial et al. |
| 8,267,935 B2 | 9/2012 | Couture et al. |
| 8,287,534 B2 | 10/2012 | Balog |
| 8,328,170 B2 | 12/2012 | Wasinger |
| 8,485,413 B2 | 7/2013 | Scheib et al. |
| 8,491,626 B2 | 7/2013 | Roy et al. |
| 8,496,603 B2 | 7/2013 | Mamourian |
| 8,555,754 B2 | 10/2013 | Chen et al. |
| 8,568,411 B2 | 10/2013 | Falkenstein et al. |
| 8,628,529 B2 | 1/2014 | Aldridge et al. |
| 8,632,553 B2 | 1/2014 | Sakamoto et al. |
| 8,702,691 B2 | 4/2014 | Weber et al. |
| 8,702,700 B2 | 4/2014 | Maeda et al. |
| 8,882,756 B2 | 11/2014 | Greeley et al. |
| 8,939,972 B2 | 1/2015 | Twomey |
| 9,023,035 B2 | 5/2015 | Allen et al. |
| 9,204,879 B2 | 12/2015 | Shelton |
| 9,320,563 B2 | 4/2016 | Brustad et al. |
| 9,326,810 B2 | 5/2016 | Shilev et al. |
| 9,345,534 B2 | 5/2016 | Artale et al. |
| 9,439,665 B2 | 9/2016 | Marczyk et al. |
| 9,445,863 B2 | 9/2016 | Batchelor et al. |
| 9,452,009 B2 | 9/2016 | Batchelor et al. |
| 9,452,011 B2 | 9/2016 | Batchelor et al. |
| 9,668,805 B2 | 6/2017 | Batchelor et al. |
| 9,707,028 B2 | 7/2017 | Batchelor et al. |
| 9,763,685 B2 | 9/2017 | Batchelor et al. |
| 9,763,730 B2 | 9/2017 | Batchelor et al. |
| 10,667,834 B2 | 6/2020 | Batchelor et al. |
| 2002/0106609 A1 | 8/2002 | Palermo et al. |
| 2002/0107517 A1 | 8/2002 | Witt et al. |
| 2002/0115997 A1 | 8/2002 | Truckai et al. |
| 2003/0018329 A1 | 1/2003 | Hooven |
| 2003/0050633 A1 | 3/2003 | Ellman |
| 2003/0097126 A1 | 5/2003 | Woloszko |
| 2003/0109876 A1 | 6/2003 | Yamauchi |
| 2003/0114850 A1 | 6/2003 | McClurken et al. |
| 2003/0144652 A1 | 7/2003 | Baker et al. |
| 2003/0181904 A1 | 9/2003 | Levine et al. |
| 2004/0030330 A1 | 2/2004 | Brassell et al. |
| 2004/0082946 A1 | 4/2004 | Malis |
| 2004/0097117 A1 | 5/2004 | Gonnering |
| 2004/0097912 A1 | 5/2004 | Gonnering |
| 2005/0065510 A1 | 3/2005 | Carmel et al. |
| 2005/0113824 A1 | 5/2005 | Sartor |
| 2005/0113825 A1 | 5/2005 | Cosmescu |
| 2005/0113827 A1 | 5/2005 | Dumbauld et al. |
| 2005/0159745 A1 | 7/2005 | Truckai et al. |
| 2005/0187512 A1 | 8/2005 | Isola et al. |
| 2005/0216019 A1 | 9/2005 | Eckman |
| 2006/0084973 A1 | 4/2006 | Hushka |
| 2006/0190035 A1 | 8/2006 | Hushka et al. |
| 2006/0217701 A1 | 9/2006 | Young et al. |
| 2007/0049922 A1 | 3/2007 | Rontal |
| 2007/0078458 A1 | 4/2007 | Dambauld et al. |
| 2007/0093857 A1 | 4/2007 | Campbell |
| 2007/0123855 A1 | 5/2007 | Morley et al. |
| 2007/0129716 A1 | 6/2007 | Daw |
| 2007/0179491 A1 | 8/2007 | Kratoska et al. |
| 2008/0033428 A1 | 2/2008 | Artale et al. |
| 2008/0077129 A1 | 3/2008 | Van Wyk et al. |
| 2008/0147092 A1 | 6/2008 | Rogge et al. |
| 2008/0154300 A1 | 6/2008 | Jabbour |
| 2008/0236860 A1 | 10/2008 | Howe |
| 2008/0287948 A1 | 11/2008 | Newton et al. |
| 2009/0062786 A1 | 3/2009 | Garito et al. |
| 2009/0062792 A1 | 3/2009 | Vakharia et al. |
| 2009/0093804 A1 | 4/2009 | Newton |
| 2009/0138003 A1 | 5/2009 | DeVille et al. |
| 2009/0138013 A1 | 5/2009 | Thorne et al. |
| 2009/0171147 A1 | 7/2009 | Lee et al. |
| 2009/0192509 A1 | 7/2009 | Curtis |
| 2009/0248002 A1 | 10/2009 | Takashino et al. |
| 2010/0042096 A1 | 2/2010 | Ellman |
| 2010/0087814 A1 | 4/2010 | Desinger et al. |
| 2010/0137854 A1 | 6/2010 | Hosier |
| 2010/0228249 A1 | 9/2010 | Mohr |
| 2011/0045680 A1 | 2/2011 | Beller |
| 2011/0054462 A1 | 3/2011 | Ellman |
| 2011/0077648 A1 | 3/2011 | Lee et al. |
| 2011/0112530 A1 | 5/2011 | Keller |
| 2011/0178515 A1 | 7/2011 | Bloom et al. |
| 2011/0224669 A1 | 9/2011 | Podany |
| 2011/0251613 A1 | 10/2011 | Guerra et al. |
| 2011/0319892 A1 | 12/2011 | Blomeyer |
| 2012/0022530 A1 | 1/2012 | Woodruff et al. |
| 2012/0078292 A1 | 3/2012 | Banju |
| 2012/0095460 A1 | 4/2012 | Rooks et al. |
| 2012/0101501 A1 | 4/2012 | Nishimura et al. |
| 2012/0123405 A1 | 5/2012 | Moua et al. |
| 2012/0123409 A1 | 5/2012 | Tohru et al. |
| 2012/0150165 A1 | 6/2012 | Conley |
| 2012/0202388 A1 | 8/2012 | Selig |
| 2012/0232553 A1 | 9/2012 | Bloom et al. |
| 2012/0310229 A1 | 12/2012 | Gregg |
| 2013/0023874 A1 | 1/2013 | Lawes et al. |
| 2013/0066317 A1 | 3/2013 | Evans et al. |
| 2013/0079762 A1 | 3/2013 | Twomey et al. |
| 2013/0178852 A1 | 7/2013 | Allen, IV et al. |
| 2013/0237982 A1 | 9/2013 | Rencher et al. |
| 2013/0296846 A1 | 11/2013 | Canady et al. |
| 2014/0100569 A1 | 4/2014 | Lawes et al. |
| 2014/0236202 A1 | 8/2014 | Palmer et al. |
| 2014/0276772 A1 | 9/2014 | Batchelor et al. |
| 2014/0276785 A1 | 9/2014 | Batchelor et al. |
| 2014/0276786 A1 | 9/2014 | Batchelor |
| 2014/0276794 A1 | 9/2014 | Batchelor et al. |
| 2014/0276795 A1 | 9/2014 | Batchelor et al. |
| 2014/0276796 A1 | 9/2014 | Batchelor et al. |

(56) References Cited

U.S. PATENT DOCUMENTS

| | | | |
|---|---|---|---|
| 2014/0276797 | A1 | 9/2014 | Batchelor et al. |
| 2014/0276798 | A1 | 9/2014 | Batchelor et al. |
| 2014/0276799 | A1 | 9/2014 | Batchelor et al. |
| 2014/0276800 | A1 | 9/2014 | Batchelor et al. |
| 2014/0276804 | A1 | 9/2014 | Batchelor |
| 2015/0119885 | A1 | 4/2015 | Windgassen et al. |
| 2015/0148798 | A1 | 5/2015 | Windgassen et al. |
| 2015/0320485 | A1 | 11/2015 | Batchelor et al. |
| 2016/0051273 | A1* | 2/2016 | Batchelor ............ A61B 18/085 606/42 |
| 2016/0051275 | A1 | 2/2016 | Batchelor et al. |
| 2016/0051314 | A1 | 2/2016 | Batchelor et al. |
| 2017/0281260 | A1 | 10/2017 | Batchelor et al. |
| 2019/0125376 | A1 | 5/2019 | Batchelor et al. |
| 2019/0126458 | A1 | 5/2019 | Batchelor et al. |

FOREIGN PATENT DOCUMENTS

| | | |
|---|---|---|
| EP | 1810629 A1 | 7/2007 |
| EP | 1977706 A1 | 10/2008 |
| JP | H08-322847 A | 12/1996 |
| JP | H09-503423 A | 4/1997 |
| JP | H09-122140 A | 5/1997 |
| JP | H10-057390 A | 3/1998 |
| JP | 2000070280 A | 3/2000 |
| JP | 2000102545 A | 4/2000 |
| JP | 2001170070 A | 6/2001 |
| JP | 2004147724 A | 5/2004 |
| JP | 2012517869 A | 8/2012 |
| WO | 96/005776 A1 | 2/1996 |
| WO | 99/66850 | 12/1999 |
| WO | 2006/122279 | 11/2006 |
| WO | 2007/002545 | 1/2007 |
| WO | 2010/101897 | 9/2010 |
| WO | 2014/096815 A2 | 6/2014 |

OTHER PUBLICATIONS

Potentially related U.S. Appl. No. 14/589,515, filed Jan. 5, 2015, published as 2015/0119885 on Apr. 30, 2015.

Potentially related U.S. Appl. No. 14/830,069, filed Aug. 19, 2015, published as 2016/0051275 on Feb. 25, 2016.

Potentially related U.S. Appl. No. 14/830,255, filed Aug. 19, 2015, published as 2016/0051314 on Feb. 25, 2016, patented as U.S. Pat. No. 9,707,028 on Jul. 18, 2017.

Potentially related U.S. Appl. No. 14/829,725, filed Aug. 19, 2015, published as 2016/0051273 on Feb. 25, 2016.

Potentially related U.S. Appl. No. 14/177,780, filed Feb. 11, 2014, published as 2014/0276794 on Sep. 18, 2014, patented as U.S. Pat. No. 9,763,730 on Sep. 19, 2017.

Potentially related U.S. Appl. No. 14/178,411, filed Feb. 12, 2014, published as 2014/0276785 on Sep. 18, 2014.

Potentially related U.S. Appl. No. 14/178,569, filed Feb. 12, 2014, published as 2014/0276804 on Sep. 18, 2014.

Potentially related U.S. Appl. No. 14/178,577, filed Feb. 12, 2014, published as 2014/0276786 on Sep. 18, 2014.

Potentially related U.S. Appl. No. 14/205,598, filed Mar. 12, 2014, published as 2014/0276795 on Sep. 18, 2014, patented as U.S. Pat. No. 9,452,011 on Sep. 27, 2016.

Potentially related U.S. Appl. No. 14/205,919, filed Mar. 12, 2014 published as 2014/0276796 on Sep. 18, 2014.

Potentially related U.S. Appl. No. 14/209,071, filed Mar. 13, 2014 published as 2014/0276798 on Sep. 18, 2014.

Potentially related U.S. Appl. No. 14/210,535, filed Mar. 14, 2014, published as 2014/0276799 on Sep. 18, 2014, patented as U.S. Pat. No. 9,452,009 on Sep. 27, 2016.

Potentially related U.S. Appl. No. 14/210,741, filed Mar. 14, 2014, published as 2014/0276800 on Sep. 18, 2017, patented as U.S. Pat. No. 9,445,863 on Sep. 20, 2016.

Potentially related U.S. Appl. No. 14/211,042, filed Mar. 14, 2014, published as 2014/0276772 on Sep. 18, 2014, patented as U.S. Pat. No. 9,668,805 on Jun. 6, 2017.

Potentially related to U.S. Appl. No. 14/206,010, filed Mar. 12, 2014, published as 2014/0276797 on Sep. 18, 2014.

Revlon Cuticle Nipper Full Jaw #38210, last accessed on eBay on Oct. 2, 2015.

Lindstrom Ergonomic Pliers, Flat Nose, Smooth Jaw—RX 7490, last accessed on Amazon on Oct. 2, 2015.

Seki Edge Flat Slant Tip Cuticle Nipper from Seki Edge, last accessed on Amazon on Oct. 2, 2015.

Red Thumb Clamp 323C Zipper Clip with a Sharp Nose Pliers from Aliexpress, last accessed on Oct. 2, 2015.

Potentially related U.S. Appl. No. 15/801,379, filed Nov. 2, 2017.

Potentially related U.S. Appl. No. 15/801,533, filed Nov. 2, 2017.

U.S. Appl. No. 15/801,379, filed Nov. 2, 2017, Bias Device for Biasing a Gripping Device by Biasing Working Arms Apart.

U.S. Appl. No. 15/801,533, filed Nov. 2, 2017, Bias Device for Biasing a Gripping Device With a Shuttle on a Central Body.

"Potentially Related U.S. Appl. No. 15/801,583, filed Nov. 2, 2017", 29 pgs.

"U.S. Appl. No. 15/801,379, Restriction Requirement dated Apr. 3, 2020", 6 pgs.

"U.S. Appl. No. 15/801,533, Non Final Office Action dated Oct. 29, 2019", 10 pgs.

"U.S. Appl. No. 15/801,533, Notice of Allowance dated Feb. 19, 2020", 9 pgs.

"U.S. Appl. No. 15/801,533, Response filed Jan. 29, 2020 to Non Final Office Action dated Oct. 29, 2019", 13 pgs.

"U.S. Appl. No. 15/801,379, Non Final Office Action dated Sep. 10, 2020", 10 pgs.

"U.S. Appl. No. 15/801,379, Response filed Jun. 3, 2020 to Restriction Requirement dated Apr. 3, 2020", 7 pgs.

"U.S. Appl. No. 15/801,379, Final Office Action dated Apr. 6, 2021", 9 pgs.

"U.S. Appl. No. 15/801,379, Response filed Dec. 10, 2020 to Non Final Office Action dated Sep. 10, 2020", 11 pgs.

"U.S. Appl. No. 15/801,379, Non Final Office Action dated Aug. 19, 2021", 18 pgs.

"U.S. Appl. No. 15/801,379, Response filed Jul. 6, 2021 to Final Office Action dated Apr. 6, 2021", 10 pgs.

"U.S. Appl. No. 15/801,379, Response filed Nov. 19, 2021 to Non Final Office Action dated Aug. 19, 2021", 14 pgs.

* cited by examiner

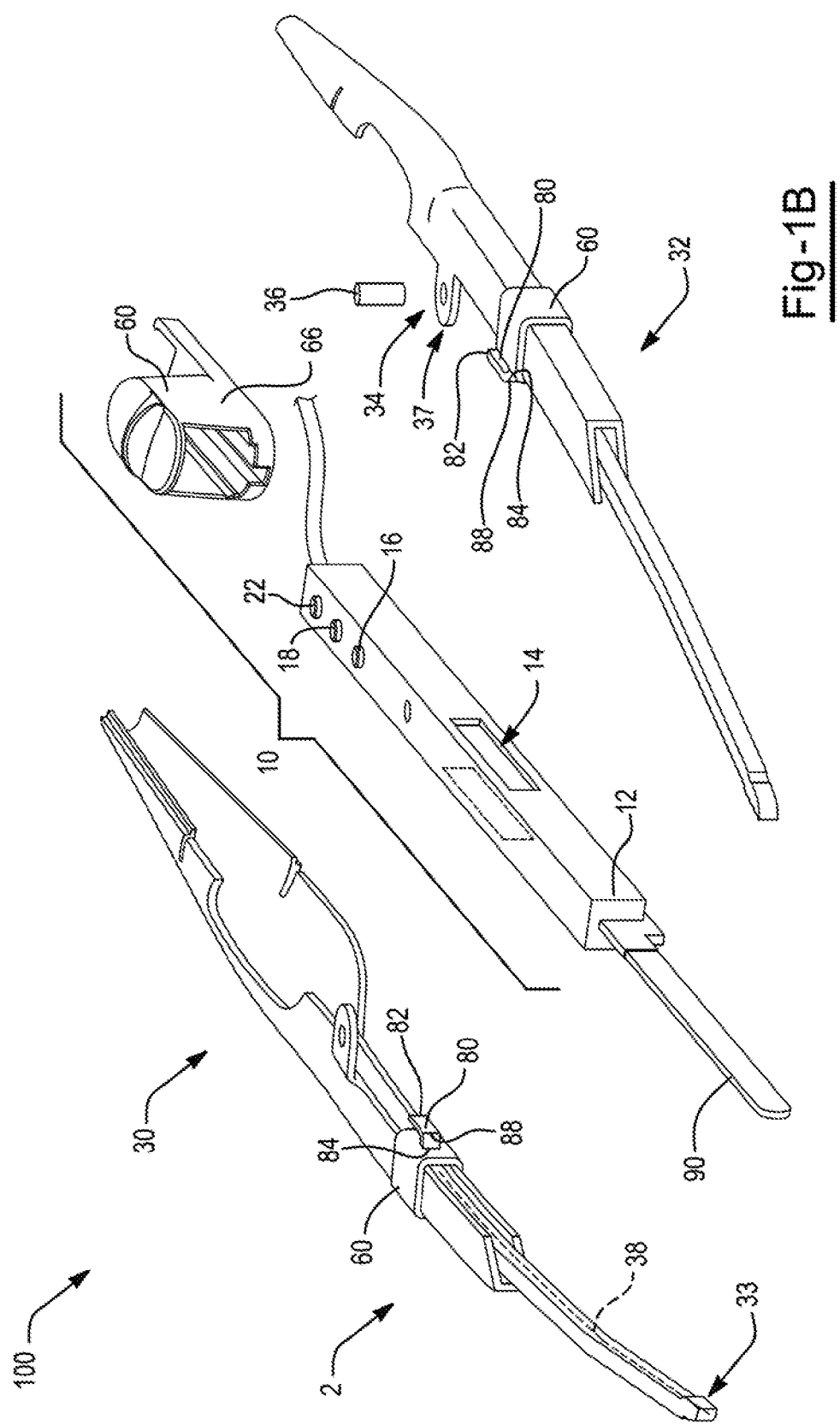

BIAS DEVICE FOR BIASING A GRIPPING DEVICE INCLUDING A CENTRAL BODY AND SHUTTLES ON THE WORKING ARMS

FIELD

The present teachings generally relate to a bias device that selectively biases the arms of a gripping device relative to a body portion and preferably a surgical device that is a combination device, which is configured as forceps that include one or more shuttles on each arm that selectively bias each arm relative to a body portion.

BACKGROUND

Typically, gripping devices such as forceps include a hinge that connects the arms together so that the arms are movable relative to each other. The hinge may allow the gripping devices to move so that the gripping devices are movable to an open position where the arms of the forceps are moved apart and upon an application of a closing force the arms of the gripping devices are moved into a closed position where an item of interest can be gripped within the gripping device. Other gripping devices such as pliers, nail cutters, cuticle nippers, or the like have added features that extend between the arms and create a direct force on both of the arms so that the arms are biased open. These devices always bias the arms apart and cannot be disconnected. Some attempts have been made to create a device that is disengageable by pivoting the device from an "on" position to an "off" position or by adding a device that is removable. However, these devices may become lost or damaged over time such that the application of force is changed or is not possible. Further, these devices impart a force directly on both of the arms so that the arms are directly moved apart by the feature.

Examples of some gripping devices such as pliers and cuticle nippers that include a feature that generates a force may be found in U.S. Pat. Nos. D386,054; 5,619,892; and 8,555,754 all of which are incorporated by reference herein for all purposes. It would be attractive to have a gripping device including a bias device that is selectively engageable. It would be attractive to have a gripping device with bias device that is engageable and disengageable without removing the bias device form the gripping device or moving the bias device on or along the gripping device. What is needed is a bias device that can be activated and deactivated with one hand. What is needed is a bias device that may apply a force to one arm individually or two or more arms. It would be attractive to have one or more bias devices where a force generated by the one or more bias devices is variable.

SUMMARY

The present teachings meet one or more of the present needs by providing: a device comprising: (a) a first working arm; (b) a shuttle, and (c) a bias device; wherein the bias device biases the first working arm when the shuttle is in a first position, and wherein the bias device is free of biasing the first working arm when the shuttle is in a second position.

The present teachings provide: a device comprising: (a) a first working arm; (b) a second working arm; (c) a shuttle, and (d) a bias device; wherein the bias device biases the first working arm away from the second arm with a first force when the shuttle is in a first position, and wherein the bias device biases the first working arm away from the second arm with a second force when the shuttle is in a second position.

The present teachings provide: a device comprising: (a) a first working arm; (b) second working arm; (c) a central body; (d) a shuttle, and (e) a first bias device (f) a second biasing device; wherein the first bias device biases the first working arm from the central body with a first force when the shuttle is in a first position, wherein the second bias device biases the second working arm from the central body and wherein the first bias device biases the first working arm away from the central body with a second force when the shuttle is in a second position.

The present teachings provide: a device comprising: (a) a first working arm; (b) a second working arm; (c) a shuttle; and (d) a bias device located on the first working arm; wherein the bias device biases the first working arm away from the second arm with a first bias force when the shuttle is in a first position, and wherein the bias device biases the first working arm away from the second arm with a second bias force or no force when the shuttle is in a second position, and the first bias force is greater than the second bias force.

The present teachings provide: a device comprising: (a) a first working arm; (b) a second working arm; (c) a shuttle; and (d) a bias device located on the shuttle; wherein the bias device biases the first working arm away from the second working arm with a first bias force when the shuttle is in a first position; and wherein the bias device biases the first working arm away from the second working arm with a second bias force when the shuttle is in a second position, and the first bias force is greater than the second bias force.

The present teachings provide: a device comprising: (a) a first working arm; (b) a second working arm; (c) a shuttle; (d) a bias device located on the first working arm; and (e) a deactivation feature located within the second working arm; wherein the shuttle covers the deactivation features when the shuttle is in a first position so that the bias device biases the first working arm away from the second working arm with a first bias force; and wherein the deactivation feature is exposed when the shuttle is in a second position so that the bias device extends into the deactivation feature so that the bias device biases the first working arm away from the second working arm with a second bias force or the bias device is free of creating a bias force.

The present teachings provide: a device comprising: (a) a first working arm; (b) a second working arm; (c) a shuttle; (d) a central body; and (e) a bias device located on the shuttle; wherein the bias device biases the first working arm away from the central body with a first bias force when the shuttle is in a first position; wherein the first bias device biases the first working arm away from the central body with a second bias force or no bias force when the shuttle is in a second position.

The present teachings provide: a device comprising: (a) a first working arm; (b) a second working arm; (c) a shuttle; (d) a central body; and (e) a bias device located on the first working arm; wherein the bias device biases the first working arm away from the central body with a first bias force when the shuttle is in a first position; wherein the first bias device biases the first working arm away from the central body with a second bias force or no bias force when the shuttle is in a second position.

The present teachings provide: a device comprising: (a) a first working arm; (b) a second working arm; (c) one or more shuttles; (d) a central body; (e) a first bias device located on the first working arm; (f) a second bias device located on the second working arm; and (g) one or more deactivation features located within the central body; wherein the one or more shuttles cover the one or more deactivation features within the central body when the one or more shuttles are in a first position so that the first working arm, the second working arm, or both are biased away from the central body with a first bias force; and wherein the one or more deactivation features within the central body are exposed when the one or more shuttles are in a second position so that the first working arm, the second working arm, or both are biased away from the central body with a second bias force or the first working arm, the second working arm, or both are not biased by the bias device.

The present teachings provide: a device comprising: (a) a first working arm; (b) a second working arm; (c) two or more shuttles; (d) a central body; (e) a first bias device located on the first working arm; and (f) a second bias device located on the second working arm; and wherein the two or more shuttles are aligned with the first bias device, the second bias device or both when the two or more shuttles are in a first position so that the first working arm, the second working arm, or both are biased away from the central body with a first bias force; and wherein two or more shuttles are misaligned with the first bias device, the second bias device, or both so that the first bias device bias the first working arm, the second bias device biases the second working arm, or both away from the central body with a second bias force or no bias force when one or all of the two or more shuttles are located in a second position.

The present teachings provide: a device comprising: (a) a first working arm; (b) a second working arm; (c) two or more shuttles; (d) a central body; (e) a first bias device located on the first working arm; (f) a second bias device located on the second working arm; (g) a first deactivation feature located on the central body that is aligned with the first bias device; (h) a second deactivation feature located on the central body that is aligned with the second bias device; and wherein one of the two or more shuttles cover the first deactivation feature within the central body when a first of the two or more shuttles are in a first position so that the first working arm is biased away from the central body with a first arm first bias force; wherein a second of the two or more shuttles cover the second deactivation feature within the central body when a second of the two or more shuttles are in a first position so that the second working arm is biased away from the central body with a second arm first bias force; wherein the first deactivation feature within the central body is exposed when the first of the two or more shuttles are in a second position so that the first working arm is biased away from the central body with a first arm second bias force or the first working arm is not biased by the first bias device; and wherein the second deactivation feature within the central body is exposed when the second of the two or more shuttles are in a second position so that the second working arm is biased away from the central body with a second arm second bias force or the second working arm is not biased by the second bias device.

The present teachings provide: a device comprising: (a) a first working arm; (b) a second working arm; (c) a central body; (d) a first shuttle located on the first working arm; (e) a second shuttle located on the second work arm; (f) a first bias device located on the first shuttle; and (g) a second bias device located on the second shuttle; wherein the first bias device biases the first working arm away from the central body with a first bias force when the first shuttle is in a first position; wherein the second bias device biases the second working arm away from the central body with a first bias force when the second shuttle is in a first position; wherein the first bias device bias the first working arm away from the central body with a second bias force or no bias force when the first shuttle is located in a second position; and wherein the second bias device bias the second working arm away from the central body with a second bias force or no bias force when the second shuttle is located in a second position.

The present teachings provide: a device comprising: (a) a first working arm; (b) a second working arm; (c) a first shuttle located on the first working arm; (d) a second shuttle located on the second working arm; (e) a central body; (f) a first bias device located on a first side of the central body; (g) a second bias device located on a second side of the central body; (h) a first deactivation feature located on the first working arm that is aligned with the first bias device; (i) a second deactivation feature located on the second working arm that is aligned with the second bias device; and wherein the first shuttle covers the first deactivation feature within the first working arm when the first shuttle is in a first position so that the first working arm is biased away from the central body with a first arm first bias force; wherein the second shuttle cover the second deactivation feature within the first working arm when the second shuttle is in a first position so that the second working arm is biased away from the central body with a second arm first bias force; wherein the first deactivation feature within the first working arm is exposed when the first shuttle is in a second position so that the first working arm is biased away from the central body with a first arm second bias force or the first working arm is not biased by the first bias device; and wherein the second deactivation feature within the second working arm is exposed when the second shuttle is in a second position so that the second working arm is biased away from the central body with a second arm second bias force or the second working arm is not biased by the second bias device.

The present teachings provide: a device comprising: (a) a first working arm; (b) a second working arm; (c) a first shuttle located on the first working arm; (d) a second shuttle located on the second working arm; (e) a central body; (f) a first bias device located on a first side of the central body; and (g) a second bias device located on a second side of the central body; and wherein the first bias device biases the first working arm away from the central body with a first bias force when the first shuttle is in a first position; wherein the second bias device biases the second working arm away from the central body with a first bias force when the second shuttle is in a first position; wherein the first bias device bias the first working arm away from the central body with a second bias force or no bias force when the first shuttle is located in a second position; and wherein the second bias device bias the second working arm away from the central body with a second bias force or no bias force when the second shuttle is located in a second position.

The teachings provide a gripping device including a bias device that is selectively engageable. The teachings provide a gripping device with bias device that is engageable and disengageable without removing the bias device form the gripping device or moving the bias device on or along the gripping device. The teachings provide a bias device that can be activated and deactivated with one hand. The teachings provide a bias device that may apply a force to one arm individually or two or more arms. The teachings provide one or more bias devices where a force generated by the one or more bias devices is variable.

BRIEF DESCRIPTION OF THE DRAWINGS

FIG. 1B is an exploded view of an electrosurgical device including forceps;

DETAILED DESCRIPTION

Figure 1A:
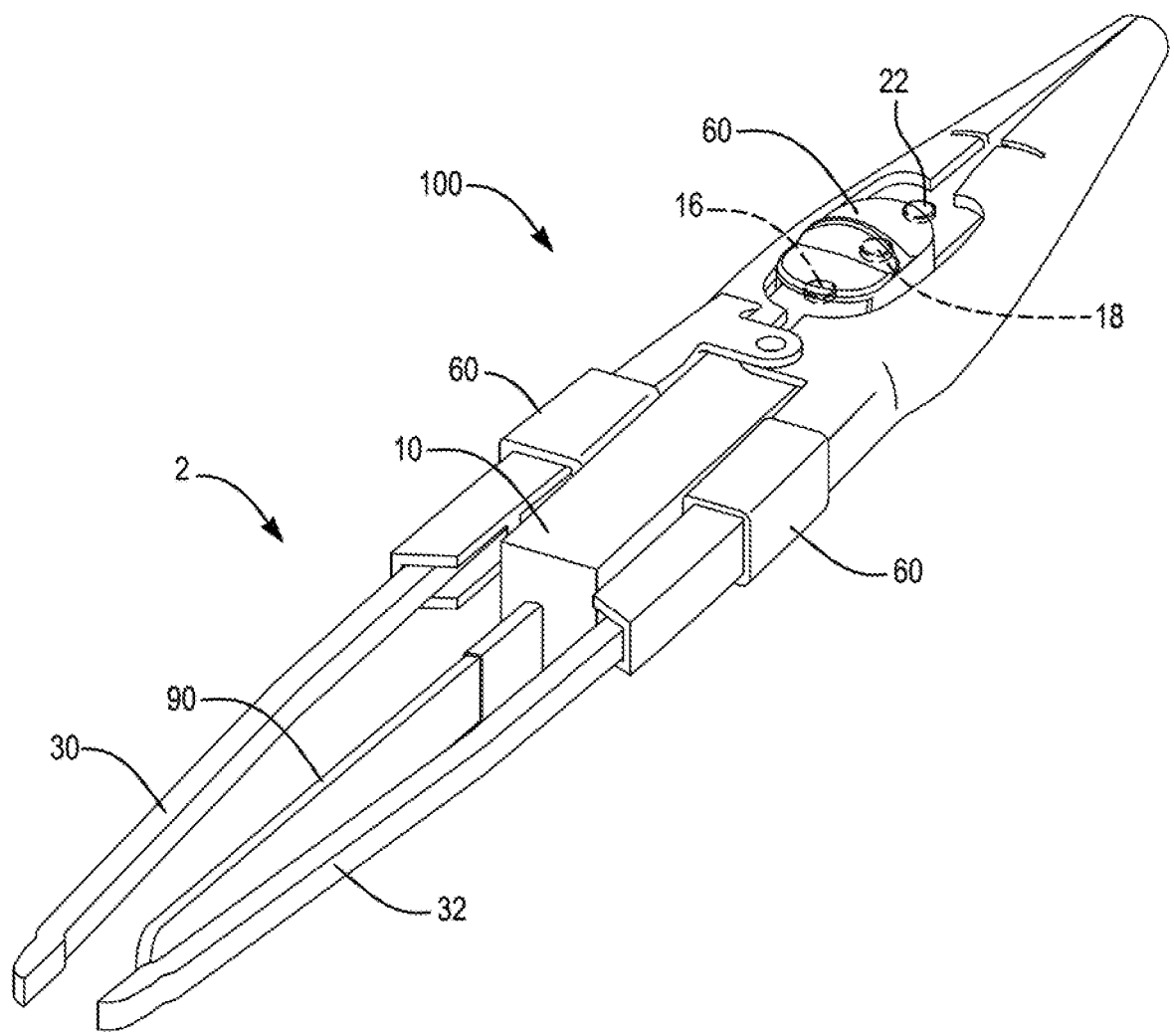
FIG. 1A is a perspective view of an electrosurgical device.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to an instrument. The instrument may function to grip one or more objects of interest. Preferably, the instrument is a gripping device. More preferably, the instrument is forceps. Most preferably, the gripping device is surgical forceps. The instrument may be forceps, tweezers, scissors, retaining ring tool, or a combination thereof. The instrument may function to grip, hold, squeeze, or a combination thereof one or more objects. The instrument may include one or more finger grips (i.e., configured like scissors) that may be used to move the instrument so that the instrument may be used to grip one or more objects. The instrument may be free of finger grips and be actuated by direct pressure being applied to opposing sides of the forceps so that the instrument closes and grips an object. The instrument may have working arms that cross and form an X shape. The instrument may be opened when a first working arm is moved towards a second working arm. The instrument may be closed when a first working arm is moved towards a second working arm. The first working arm and the second working arm may move laterally, within a plane, or both (e.g., perpendicular to a longitudinal axis). Preferably, the first working arm and the second working arm move towards and away from each other without rotating, moving out of a plane, or both. The instrument has a distal end and a proximal end. The instrument may have working arms that are generally straight. The instrument includes at least two working arms.

The working arms may function to grip, hold, squeeze, or a combination thereof an object when the object is between the two or more opposing working arms. The working arms include a proximal end and a distal end. The proximal end may be in contact with a body, a handle, or both. The first working arm and the second working arm may converge together at their respective proximal ends, at the handle, the body, or a combination thereof. The distal end may include one or more electrodes, one or more tips, or both for applying a therapy current, a gripping force, or both. The working arms may include one or more gripping features that may assist in gripping, holding, squeezing, or a combination thereof an object. The instrument may include two or more working arms. Preferably, the instrument includes at least two working arms. The instrument may include three or more, four or more, five or more, or even six or more working arms. More preferably, the instrument only includes two working arms. The working arms may all be substantially identical. When only a first working arm and a second working arm are present the first working arm and the second working arm may be mirror images of each other. When only a first working arm and a second working arm are present the instrument is configured as forceps.

The working arms, forceps, electrosurgical device, or a combination thereof may be movable between at least a first position and a second position. For example, in the second position the working arms are immobilized so that the working arms cannot be used a forceps. The working arms, blade, or both may have a first position and a second position; however, the shuttles may have a plurality of positions along the working arms, the blade, the body, or a combination thereof. The working arms may be longitudinally static and moveable relative to each other (e.g., laterally within a plane). The working arms may be longitudinally moveable and may be moveable relative to each other (e.g., laterally movable) so that a gripping force may be created. Preferably, the working arms may be movable laterally relative to each other (i.e., towards and away from each other within a single plane). The working arms may not be rotatable. The working arms may rotate about a pivot or a pivot pin to grip or create a force. A pin may connect a first working arm and a second working arm and the pin may be the pivot point. The working arms may be movable about a pivot point so that as one end of the working arms are moved closer together (e.g., a proximal end) an opposing end is moved further apart (e.g., a distal end). The working arms may each have a pivot point. The working arms may extend cantilever and may pivot about a cantilever connection with the body, the handle, the gripping portion, or a combination thereof. The working arms may be retractable and/or extendable individually, simultaneously, or both. The working arms may be selectively retractable and/or extendable so that one or more tip regions are exposed. The working arms may be rigid. The rigid working arms may rotate about a pivot or a pin to create a gripping force. The working arms may be connected to each other, a body portion, or both by a pin that extends through a pivot and the working arms may rotate about the pivot to create a gripping force. The working arms may include one or more cross overs.

The one or more cross overs may function to change the forceps from a bias open device to a bias closed device. The cross overs may be where the working arms cross each other so that a distal end of the working device is located on an opposing side of the forceps as a working arm that it was connected, a proximal end, or both. The cross over may have one working arm passing over or under another working arm. The cross over may have a portion of one working arm passing through another working arm. The cross over may form an X shape. The cross over may be located on an opposite end of the arms as the one or more bosses, the pivot point, or both.

The working arms may include one or more bosses that a pin extends through to connect the working arms to body so that a pivot point is created. Preferably, each working arm includes at least two bosses and the bosses extend on both sides of a portion of the body and the pivot pin extends through the bosses and a portion of the body to connect the arms to the body. The pivot pin may movably connect the working arms to a body. The pivot point may create a hinge. A single pivot pin may connect more than one working arm. For example, the working arms may be connected together by a single pivot pin. Each working arm may be connected individually by a pivot pin. The connection may form a joint. The joint may be a pivot joint, a cantilever joint or both. Each working arm may include a joint. Both working arms may be connected by a single joint. The bias device may be located on a distal side of the joint or the proximal side of the joint. The first working arm, second working arm, and body may all be part of the joint. The first working arm and body and the second working arm and body may form a joint. The pivot pin may be made of any material that permits the working arms to rotate. For example, the pivot pin may be plastic, metal, stainless steel, surgical steel, or a combination thereof. The working arms may be free of a pivot pin. For example, a first working arm may extend over (e.g., cross-over or cross-under) a second working arm so that the distal end is located on an opposing side of the forceps and the proximal end. The cross-over/cross-under may create a device that opens upon an application of force. The working arms may be flexible and may flex to open and close. For example, the working arms may be constrained (at one end) and upon release of the constraint the working arms may flex open. The working arms may be movable between two or more positions. Preferably, the working arms are movable between at least a first position (e.g., open) and a second position (e.g., closed). The working arms may be movable between a bipolar configuration (e.g., first position) and a monopolar configuration (e.g., second position). The working arms may be movable between an open position (i.e., first position) and a closed position (i.e., second position). The working arms in the first position may be off, energized, one working arm may be energized, or a combination thereof. The working arms in the second position may be off, one or both of the working arms may be electrically disconnected, one or both of the working arms may be electrically connected, one working arm may be shorted by the other working arm, or a combination thereof. The working arms may be moved between one or more positions by a user applying a force to a gripping portion.

The gripping portion may function to open the working arm, close the working arms, allow a user to manipulate the forceps, or a combination thereof. The gripping portions may move the working arms when a force is applied to the working arms. The gripping portions may be located at the proximal end or the distal end of each of the working arm. The gripping portion may be located proximate to the handle, the body, or both. The gripping portion of the working arms may extend over the handle, the body, or both. The gripping portions may extend along the handle, the body, or both. The gripping portions may be located opposite a tip region of the working arms. The gripping portions may be located at a proximal end and the tip region may be located at a distal end.

The working arms may include a tip region. The tip region may include a portion that is configured to assist in facilitating gripping, holding, squeezing, or a combination thereof. The tip region may be located at the distal most end (i.e., an end of the instrument furthest from the user) of the working arms. The tip regions when moved towards each other may grip an object of interest between the two working arms (e.g., tissue). Additionally, the tip region may be configured in one or more electrosurgical configurations (e.g., a monopolar configuration, bipolar configuration, or a combination of both). The tip region may include teeth, serrations, mouse teeth, be free of teeth (i.e., smooth), or a combination thereof. The tip region may be fully and/or partially insulated. Preferably, the tip region includes insulation on the non-contact portions of the working arms so that electrosurgical energy is not transferred through incidental contact. The tip region may include or may be an active portion (e.g., an electrode), an inactive portion (e.g., an insulated portion), or a combination of both.

The electrode may function to provide a therapy signal (e.g., current, voltage, power, electricity, or a combination thereof) to a location of interest. The electrode may be electrically conductive so that the instrument is an electrosurgical device. The electrode may transmit a therapy signal between the working arms, from a working arm to the blade, from a working arm to the blade electrode, from one or both working arms to a ground pad, from a blade to a ground pad, or a combination thereof. The electrode may both provide power and a contact surface for gripping and holding an item of interest. The electrode may be connected to an electrical path that provides a therapy signal from the body, a generator, or both to a location of interest.

The electrical path may function to provide a therapy signal to a feature or location of interest. The electrical path may extend along one or more of the working arms. The electrical path may be one or more structures that when connected together provide a path for power to flow through the instrument. The electrical path may extend along a blade. The electrical path may be engageable and disengageable. The electrical path may extend from a handle, gripping portion, body, or a combination thereof to the working arms (e.g., first working arm, second working arm, or both), and/or the blade (which may include a blade electrode).

The blade may function to mechanically cut, electrically cut, electrically coagulate, apply a therapy current, or a combination thereof. The blade may be any device that may be used to apply monopolar power during a procedure, that may be longitudinally movable, rotationally movable, extendable, retractable, or a combination thereof. The blade may be movable along or relative to a handle, a body, a gripping portion, or a combination thereof. The blade may be connected to and extend from a handle, a body, a gripping portion or a combination thereof. The blade may be static. Preferably, in one embodiment the blade may be static and the working arms moved relative to the blade so that when the working arms are moved the blade is exposed. More preferably, the blade is a movable. The blade may have one or more positions. The blade may have a plurality of positions. The blade may have a first position (e.g., retracted), a second position (flush), and a third position (e.g., extended). The first position may be where the blade is located relative to the working arms so that the working arms are past the blade (e.g., the blade is retracted so that the working arms extend past the blade or the working arms are extended so that the working arms extend past the blade). The first position may be where the blade is electrically disconnected, electrically shorted relative to another handpiece component, electrically insulated so that power cannot pass from the blade, or a combination thereof. The second position may be where a distal end of the blade is flush with the distal end of the first working arm, the second working arm, or both. The third position may be where the blade is located relative to the working arms so that the blade is extended beyond the working arms (e.g., the blade is extended so that the working arms are located proximate to the user or the working arms are retracted so that the blade is beyond the working arms). The second position and/or third position may be where the blade is electrically connected, supplies a therapy current, is electrically continuous, or a combination thereof. The blade may be a separate piece that when activated may be used to supply monopolar power. The blade may be formed by connecting the two working arms together and supplying power through only one working arm. The blade may be used for electrically cutting, mechanically cutting, or both. The blade may be a discrete third working arm that may extend from one of the working arms, between the working arms, or both. Preferably, the blade extends from the body. The electrosurgical device may be free of a blade. The blade may include or be a blade electrode. The blade electrode may supply a therapy current to a location of interest. The blade electrode may contact tissue so that a therapy current is supplied from the blade electrode to the first working arm, second working arm, ground pad, or a combination thereof. One or more shuttles may move relative to the blade, along the blade, parallel to the blade, or a combination thereof. Preferably, the shuttle is free of movement along the blade. The blade may be connected to a shuttle that may move the blade.

The one or more shuttles may function to activate or deactivate one or more functions of the instrument, move one or more components of the instrument, obstruct one or more buttons of the instrument, move a bias device, move a deactivation feature, deactivate a deactivation feature, align a bias device and deactivation feature, align a bias device and a contact zone, or a combination thereof. The shuttle may be connected to or move along a body, a handle, a first working arm, a second working arm, a blade, or a combination thereof. The one or more shuttles may move independent of the first working arm, the second working arm, the blade, the body, or a combination thereof. For example, if the blade is longitudinally movable, a shuttle located on the body may move longitudinally without the blade moving or vice versa. The electrosurgical device may include one or more shuttles, two or more shuttles, three or more shuttles, four or more shuttles, or even five or more shuttles. For example, there may be three shuttles on the body, one that moves the blade and two that move along the body to activate and deactivate bias, and each working arm may include a shuttle. Each working arm may include one or more shuttles. The body, blade, or both may include one or more shuttles. The body may include two shuttles or even three shuttles. The shuttles may function to carry one or more bias devices. The shuttles may function to carry one or more deactivation features. The shuttles may only have one or more bias devices, one or more deactivation features, one or more contact zones, or a combination thereof on one side. For example, a shuttle may only face a first side of a body or a first working arm. The shuttle may have two sides and each side may include one or more deactivation features, one or more bias devices, one or more contact zones, or a combination thereof. The shuttles may include two or more bias devices, contact zone, deactivation features, or a combination thereof on each side so that as the shuttle is longitudinally moved the amount of force created may be varied based upon the distance of the shuttle from pivot point, body, or both. The shuttle may have two or more pieces. The shuttle may be a plurality of pieces. The shuttle may have a first shuttle first portion, a first shuttle second portion, a second shuttle portion (including one or more portions), a third shuttle portion (including one or more portions (e.g., a third shuttle first portion and a third shuttle second portion)), a fourth shuttle portion, or a combination thereof. For example, two shuttle portions may be located on the body and the two shuttle portions may be moved as one shuttle or moved as two discrete shuttles. Three shuttles may be located on the body. The three shuttles may be a first shuttle first portion and a first shuttle second portion and a second shuttle portion. The first shuttles may control bias and the second shuttle may control the blade position. A first shuttle first portion may be located on a first working arm and a first shuttle second portion may be located on a second working arm. A first shuttle portion may be located on a first side of the body and a second shuttle portion may be located on a second side of the body. The shuttle may function to provide a contact zone or contact location for one or more bias devices. The shuttle may be movable between a plurality of positions. The one or more shuttles may be movable between one or more positions. Preferably, the shuttle is movable between at least a proximal position (e.g., first position) and a distal position (e.g., second position). The shuttle may retract and extend the blade, a working arm, or both. The shuttle may engage and disengage one or more bias devices. The shuttle may cover, expose, or both one or more deactivation features, one or more buttons, or both. Each shuttle may include two or more positions, three or more positions, four or more positions, or even five or more positions. The shuttle may move along a body portion. The shuttle may move along one or more of the working arms. The shuttle may extend along or around one or more sides of the body portion. Preferably, the shuttle extends around at least one or more sides of the body portion. The shuttle may engage the bias device. The shuttle may engage the bias device when the shuttle is in the first position, the second position, the third position, the fourth position, or a combination thereof. The shuttle may be free of engagement with the bias device when the shuttle is in the first position, the second position, the third position, the fourth position, or a combination thereof. The shuttle may have one or more contact zones that are contacted by the bias devices.

The one or more contact zones may function to create a contact surface for the bias device to contact. The one or more contact zones may function to assist is biasing the working arms. The one or more contact zones may be any area of the instrument where the bias device contacts to create a bias force. The one or more contact zones may be a region of the shuttle, the one or more of the working arms, body, or a combination thereof that assists in biasing the working arms. For example, the bias device may be connected to the working arms and may contact a contact zone of the shuttle. In another example, the bias device may be connected to a shuttle and may contact a contact zone of the working arms. The one or more contact zones may either engage the bias device or be free of engagement with the bias device. The one or more contact zones may be generally planar. The one or more contact zones may have one or more steps that extend in different planes so that contact with each step varies the amount of force created by the bias device. For example, movement of a shuttle or a bias device may move from a first step to a second step or even a third step which may increase or decrease an amount of force created by the bias device. The one or more steps may change the thickness of the shuttle so that compression of the bias device varies the amount of generated by the bias device. When steps are present the shuttle may have a position that corresponds to each of the steps. The force may be sufficiently low so that finger pressure may overcome the force to bias the working arms. The force may be about 1 Kg or more, about 2 Kg or more, about 5 Kg or less, or about 3 Kg or less (i.e., between about 0.5 Kg and about 2 Kg). The amount of force may be varied by moving one or more shuttles, bias members, or both toward a distal end, towards a proximal end, towards a pivot point, towards a cross over, a combination thereof. The shuttle may be distally or proximally moved to vary the bias force provided to each working arm depending upon a longitudinal location of the shuttle. The bias device may provide a force that is close to zero but greater than a zero bias force. The shuttle may have a distal position, a first position, a second position, a third position, a proximal position, or a combination thereof. The contact zones may have one or more recesses so that when a portion of a bias device (e.g., a free end or contact portion) contacts the contact zone the bias device and shuttle form at least a temporary connection. The one or more recesses may substantially prevent the bias device from moving (e.g., sliding) along the contact zone (e.g., the bias device may move 1 mm or less relative to the contact zone). The contact zone may be curved, include a detent, be flat, disc shaped, or a combination thereof. The contact zone may be moved so that the bias device is free of contact with the shuttle and the bias device is disabled.

The bias device may function to move one or more of the working arms. The bias device may bias one or more of the working arms open (i.e., away), one or more of the working arms closed (i.e., towards), or both. The bias device may bias one or more of the working arms off of a body, a shuttle, a handle, an inner shell, a contact zone, or a combination thereof. The bias device may be free of providing a bias (e.g., the bias device may be disabled, turned off, or both). The bias device may longitudinally movable (e.g., along a length of the electrosurgical device), laterally movable (e.g., move with a working arm along a plane that is at an angle relative to the length (e.g., perpendicular)), rotationally movable (e.g., around a working arm), or a combination thereof. The bias device may be longitudinally static. The bias device may be fixed to a working arm, body, shuttle, first shuttle portion, second shuttle portion, third shuttle portion, handle, gripping portion, or a combination thereof. The bias device may be made of plastic, metal, rubber, or a combination thereof. The bias device may extend between a first working arm and the body, a second working arm and the body, or both. Depending on the position of the shuttle the bias device may be opposing a working arm or a body. The bias device may be made of an elastic material. The bias device may include elastomeric characteristics. The bias device may be a spring. The bias device may be a leaf spring, a cantilever spring, a helical spring, compression spring, a coil, a helical extension, or a combination thereof. The bias device may include one or more constrained ends, one or more free ends, one or more contact portions, or a combination thereof.

The one or more constrained ends may function to connect the bias device to a part of an instrument. The one or more constrained ends may permanently connect the bias device to a part of an instrument. The one or more constrained ends may removably connect the bias device to a part of an instrument. The one or more constrained ends may be a single constrained end. The one or more constrained ends may be located on opposing ends of the bias device. For example, two opposing ends of the bias device may be constrained and a middle section may extend outward to provide the bias. The one or more constrained ends may not be an end but may constrain the bias device between to a part of the instrument at a location between the ends. For example, a central section may be constrained and two portions may extend outward from the constrained central section. The one or more constrained ends preferably are located at an end that is towards the distal end of the device. For example, the bias device may include a distal end and a proximal end and the constrained end may be the distal end of the bias device. The constrained end may be connected to a working arm, the shuttle, a body, handle, gripping portion, or a combination thereof. The first working arm and the second working arm may each be connected to a constrained end of a bias device. The bias device may extend outward from the constrained end. For example, the bias device may extend from a constrained end on a first working arm towards a second working arm. The constrained end may form a cantilever connection. The bias device may only be connected at the constrained end and may include a free end that is not constrained to any part of the instrument (i.e., the working arms or the shuttle).

The free end may function to contact one or more parts of the instrument to create a bias force. The free end may extend away from the constrained end but may be free of contact with another part of the instrument to create the bias force. For example, the free end may extend outward and contact the same part as the constrained end (e.g., an arm, shuttle, body) and a contact surface between the free end and the constrained end may create the bias force. The free end may extend towards the same part of the instrument as the bias device (e.g., the shuttle, a working arm, body). Preferably, the free end contacts a contact zone and assists in creating the bias force. The free end may move along a portion of the instrument as the contact portion is biased. The free end may be in contact with a part of the instrument and move as the working arms are moved towards each other. The free end may be substantially static during movement of the working arms towards each other so that energy is stored within the bias device. The free end may be opposite a constrained end (e.g., cantilever connection). The free end may be in the same plane as the constrained end. The free end may be in a different plane than the constrained end. The bias device may include more than one free end. For example, the bias device may include 2, 3, 4, 5, or more free ends. Preferably, the bias device includes a single free end. The free end may be flat. The free end may include a covering or another material. The free end may include an insulator, an elastomeric material, or both. The free end may be free of any other materials. The free end and the constrained end may be separated by one or more breaks.

The one or more breaks may function to store energy. The one or more breaks may function to move the bias device from a first plane to a second plane. The one or more breaks may be one or more arcuate portions of the bias device. The one or more breaks may be one or more bends in the bias device. The one or more breaks may allow the bias device to follow the contour of the working arms, the shuttle, a portion of the instrument, or a combination thereof. The one or more breaks may be a shaped portion of the bias device. The one or more breaks may move when the working arms move towards each other and store energy and when a pressure is released the working arms may release the stored energy and bias the working arms apart. The one or more breaks extend the bias device from a constrained end towards a contact portion. The one or more breaks may strengthen a portion of the bias device. The one or more breaks may prevent one or more portions of the bias device from moving. The one or more breaks, bias device, or both may include the contact portion.

The one or more contact portions may function to contact another portion of the instrument to bias one or more of the working arms apart or bias one or more of the working arms together. Preferably, the contact portions of the bias device contact a contact zone on a working arm, the shuttle, a body, or a combination thereof. The one or more contact portions may contact a first working arm, a second working arm, a shuttle, a body, or a combination thereof. The one or more contact portions may contact a piece adjacent to a working arm. The one or more contact portions may contact a working arm. For example, the bias device may be connected to a first working arm and the contact portion may contact the first working arm and a second working arm or a shuttle to create a bias force. The contact portion may assist in compressing a bias device so that energy is stored within the bias device. The contact portion may assist in releasing energy so that the first working arm and second working arm are moved apart. Each bias device may have one or more contact portions. Each bias device may include two or more contact portions. For example, each bias device may include a contact portion that contacts a first part of the instrument (e.g., an arm) and second part of the instrument (e.g., another arm or a shuttle). The contact portion may be a constrained end, a free end, or both. The contact portion may contact a shuttle, a body, or both of the instrument. The contact portion may contact a shuttle when a shuttle is in a first position (or distal position) and may extend into a body, into a deactivation feature, or both and be free of contact with the contact zone when the shuttle is in a second position (or proximal position).

The body may function to serve as the primary gripping region for a user. The body may be a central body. The body may connect all of the components together (e.g., the blade, working arms, shuttle, buttons, etc. . . . ). The body may be or include a handle, a gripping portion, or both. The body may house electrical components, buttons, controls, or a combination thereof. The body may receive power, therapy signals, or both from a generator. The body may be connected to the working arms by a pivot pin, bosses, or both. The body may connect to a proximal end of each of the working arms. The body may extend between two or more working arms. The working arms may pivot about the body and the body may remain substantially static. Each working arm may move relative to the body individually. The body may connect both of the working arms together so that the working arms move with each other. The body portion may carry the shuttle. The body portion may have a track that the shuttle moves along. The body portion may include an opening that receives all or a portion of the blade. For example, the blade may move in and out of the body portion. The shuttle may be part of the body portion and the shuttle may cover a portion of an inner shell of the body portion. The body may be covered by an inner shell.

The inner shell may extend around the body portion, a portion of the one or more working arms, or both. The inner shell may cover one or more surfaces, preferably two or more surfaces, and more preferably three or more surfaces. The inner shell of the body portion may function to support the shuttle, the activation buttons, connect the working arms, receive all or a portion of the bias device, receive all or a portion of the blade, or a combination thereof. The inner shell may house all of the electrical elements. The inner shell may assist in activating or deactivating one or more electrical functions of the instrument. The inner shell may function to be a piece that a user grips. The inner shell may include one or more deactivation features.

The one or more deactivation features may function to deactivate the bias device, deactivate an electrosurgical configuration, or both. The one or more deactivation features may be a hole or recess that extends through one or more walls of the inner shell, body portion, working arm, handle, gripping portion, shuttle, electrosurgical device, or a combination thereof. Preferably, the deactivation features are a recess that create a gap so that the bias device cannot contact a part of the device to create a bias force. The one or more deactivation features may be located in a first working arm, second working arm, first shuttle, second shuttle, or a combination thereof. One or more parts may include two or more or even a plurality of deactivation features. For example, a shuttle may include two deactivation features and two contact zones. The one or more deactivation features may be one or more recesses, one or more openings, one or more through holes, or a combination thereof. For example, the inner shell may include a recess so that when the shuttle is in a proximal position the recess is exposed and one or both of the bias devices extend into the recess and are free of contact with the inner shell and one or both of the bias devices are deactivated. The one or more deactivation features may be a distance between a contact zone and a contact portion. For example, when the shuttle is moved from a first position, where the contact zone and the contact portion are in contact, to a second position, the contact portion may be located too far from the contact zone to create a bias force. The one or more deactivation features may be a gap that is greater than a distance between a bias device and a contact surface so that the bias device cannot create a bias force. The deactivation features may be a hole that the bias device extends into so that the bias device cannot bias. The one or more deactivation features may be located on the shuttle or in the shuttle so that when the shuttle is in one position one or both of the bias devices align with the deactivation feature and are deactivated and when the shuttle is in a different position the bias device aligns with a contact zone and is activated. Preferably, the deactivation features are aligned with the contact portions of the bias device. More preferably, the deactivation features, activation buttons, or both are covered and uncovered by the shuttle moving between positions.

The first activation button, second activation button, or both may function to enable one or more electrical configurations of the instrument. The first activation button, second activation button, or both may provide a therapy current to one or both working arms, the blade, or both. The activation buttons may allow for the instrument to be an electrosurgical device. The activation buttons may allow the instrument to be both a mechanical gripping device and an electrosurgical device.

The present teachings relate to an instrument that may include electrical elements and be an electrosurgical device. Preferably, the present teachings relate to an electrosurgical device and associated componentry that form an electrosurgical system. The electrosurgical system may be any system that includes one or more of the devices taught herein. Preferably, the electrical surgical system includes at least an electrosurgical device. The electrosurgical system may include one or more handpieces (i.e., a body) as taught herein, one or more ground pads, one or more generators, one or more electrosurgical devices, one or more adjacent handpiece components, or a combination thereof and the teachings herein of each device which are incorporated into the electrosurgical system. The electrosurgical device may be any device that may be used by a surgeon to perform a surgical procedure. The electrosurgical device may function to be switched between two or more configurations, two or more states, or both (e.g., be a combination device). For example, the electrosurgical device may be switched between a monopolar configuration, a bipolar configuration, a non-electrosurgical configuration, or a combination of the three. The electrosurgical device may be any device that may be switched between two or more configurations with one hand so that a user may switch between the configurations without the need for a second hand, without disrupting the procedure, or both. The electrosurgical device may be any device and/or configuration that may be used ambidextrously, ambidextrously switched between configurations, or both. The electrosurgical device may be used to cut, perform hemostasis, coagulate, desiccate, fulgurate, electrocautery, or a combination thereof. The electrosurgical device may be any device that includes bipolar capabilities, monopolar capabilities, non-electrosurgical capabilities, or a combination thereof. The electrosurgical device may be used in open surgery. In addition to its electrosurgical capabilities the electrosurgical device may be used for non-electrosurgical purposes. For example, the electrosurgical device may be used as forceps, tweezers, or both that may be used to grip an object, an organ, a vein, skin, tissue, the like, or a combination thereof. In another example, one or more parts of the device may include a sharp edge and may be used to cut, similar to that of a scalpel. The electrosurgical device includes a proximal end (e.g., an end proximate to a user) and a distal end (e.g., an end furthest from a user). The electrosurgical device may include a handpiece and a generator. The electrosurgical device may have one or more therapy signals that extend between the handpiece and the generator.

The one or more therapy signals may be a signal, power, continuity, or a combination thereof. The one or more therapy signals may extend from and/or to the handpiece (e.g., blade, working arms, or both). The one or more therapy signals may be formed by the handpiece, formed by the generator, or both. The electrosurgical therapy signals may be a therapy current. Preferably, the electrosurgical therapy signals indicate that a user has performed a step and a signal is being transmitted so that therapy current, energy, or both is generated. The electrosurgical therapy signals may provide a signal so that one or more therapy currents are produced and the therapy currents may be used for electrosurgery. The electrosurgical therapy signal may be a monopolar therapy signal, a bipolar therapy signal, or both. The electrosurgical therapy signal may be a monopolar therapy signal, a bipolar therapy signal, or both. The monopolar therapy signal may be any signal that has a voltage differential between a return port and an active port in the generator. The monopolar therapy signal may be any signal that when applied by the electrosurgical device extends from one pole of an electrosurgical device to another pole located at a remote location, off of the electrosurgical device, off the handpiece, or a combination thereof. The bipolar therapy signal may be any signal that has a voltage differential between two leads that are connected to the electrosurgical device, that are located in the generator, or both. The bipolar therapy signal may be any signal that when applied by the electrosurgical device extends from one component of a handpiece to another component of the handpiece (e.g., between two working arms, from a blade to one or both working arms, or both). An electrosurgical therapy signal, when the activation circuit is in the second state, may exit the handpiece so that a therapy current extends from a blade, between the first working arm and the second working arm, between the blade and one or both of the working arms, or a combination thereof. The therapy signal may be generated and conducted from the handpiece to the generator.

FIG. 1A is a perspective view of and electrosurgical device 100 configured as forceps 2 with a blade 90. The blade 90 is retracted between the first working arm 30 and the second working arm 32 so that the working arms 30 and 32 are movable. The blade 90 is connected to a body 10 that carries a shuttle 60 and a first activation button 16, second activation button 18, and third activation button 22. The first working arm 30 includes a shuttle 60 and the second working arm 32 includes a shuttle 60 and the shuttles each carry a bias device (not shown) that selectively bias the first working arm 30 and second working arm 32 respectively against the body 10.

FIG. 1B illustrates an exploded view of the forceps 2. The forceps 2 as shown are also an electrosurgical device 100. The forceps 2 include a body 10 with a blade 90 extending therefrom. The body 10 is partially covered by a movable shuttle 60 (e.g., a second shuttle portion), which moves between a first position (not shown) and a second position (not shown). The first working arm 30 and the second working arm 32 are substantially a mirror image of each other. Both the first working arm 30 and the second working arm 32 include a pivot 37 with a pivot point 36, which as shown is a pin, that the working arms move about to create a gripping force. The pivot point 36 extends through a pair of opposing bosses 34 on each of the working arms. Each of the working arms include a bias device 80, riding on a shuttle 60 (e.g., a first shuttle first portion and a first shuttle second portion), that assists in opening the working arms 30, 32. The bias devices 80 includes a free end 82 and a constrained end 84. The free end 82 contacts a contact zone 66 of the shuttle 60 when the shuttle 60 is in a first position. The bias devices 80 include breaks 88 that assist in resiliently biasing the working arms 30, 32. Each of the working arms 30, 32 include an electrical path 38 so that power travels to electrodes 33 at ends of each respective working arm 30, 32. The body 10 includes a first activation button 16, a second activation button 18, and a third activation button 22. The body 10 has a deactivation feature 14, which as shown is a through hole, in the inner shell 12 of the body 10.

Figure 2:
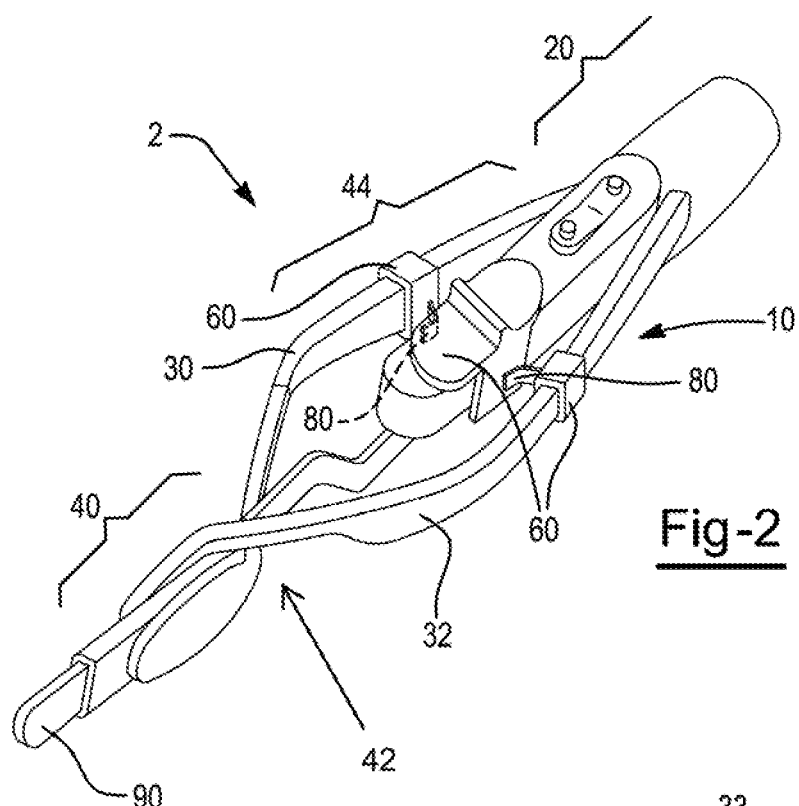
FIG. 2 is a perspective view of an electrosurgical device with forceps that are bias closed.

FIG. 2 illustrates forceps 2 where the first working arm 30 and the second working 32 include a cross over 42 so that distal ends of the first working arm 30 and the second working arm 32 are biased closed. The forceps 2 include a body 10 having handle 20 connected to a gripping portion 44 with a distal end 40 extending beyond the gripping portion 44. When a force is applied to the gripping portion 44 of the first working arm 30 and the second working arm 32, the first working arm 30 and the second working arm 32 are biased towards the body 10 and ends of the first working arm 30 and the second working arm 32 open. Once the force is released the bias devices 80 on the shuttles 60 bias the working arms 30, 32 closed by the bias devices 80 biasing off of the shuttle 60 on the body 10. A blade 90 is connected to the shuttle 60 so that movement of the shuttle moves the blade 90 between the first working arm 30 and the second working arm 32 towards and away from the distal end (i.e. the tip) 40. As shown, the blade 90 is extending beyond the first working arm 30 and the second working arm 32.

Figure 3:
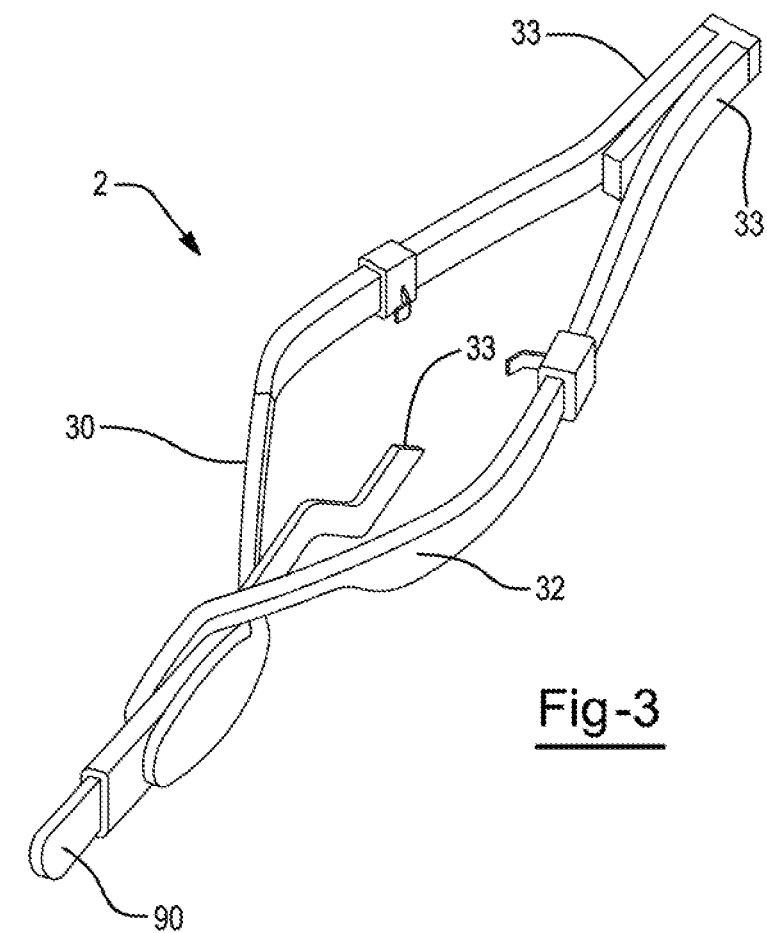
FIG. 3 illustrates the forceps of FIG. 2 with the body removed.

FIG. 3 illustrates of the forceps 2 of FIG. 2 with the body removed. With the body removed, the first working arm 30, the second working arm 32, and the blade 90 are fully visible. Ends of the first working arm 30 and the second working arm 32 are connected together to assist in creating a bias force. An electrode 33 is located at ends of the first working arm 30 and the second working arm 32 so that bipolar energy can be supplied between the first working arm 30 and the second working arm 32. An electrode 33 is located on the blade 90 so that monopolar energy can be supplied through the blade 90.

Figure 4:
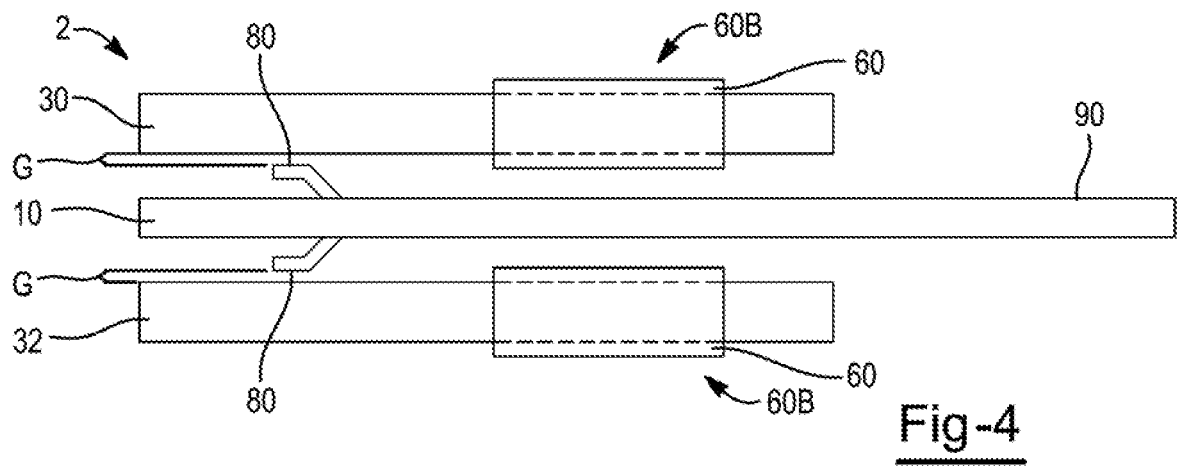
FIG. 4 is a plan view of forceps including two shuttles in a second position.

FIG. 4 illustrates the forceps 2 with a first working arm 30 and a second working 32 with a body 10 located therebetween. A bias device 80 is located on a first side of the body 10 proximate to the first working arm 30 and a bias device 80 is located on a second side of the body 10 proximate to the second working arm 32. The body 10 is in communication with a blade 90 that is extended distal of the first working arm 30 and the second working arm 32. The first working arm 30 and the second working arm 32 both include a shuttle 60 that are located in a second position 60B so that a gap (G) is located between the first working arm 30 and the bias device 80 on the first side of the body 10 and a gap (G) is located between the second working arm 32 and the bias device 80 on the second side of the body 10. The gaps (G) are sufficiently large so that the first working arm 30 and the second working arm 32 are not biased by a respective bias device 80 when a force is applied to the first working arm 30 or the second working arm 32.

Figure 5:
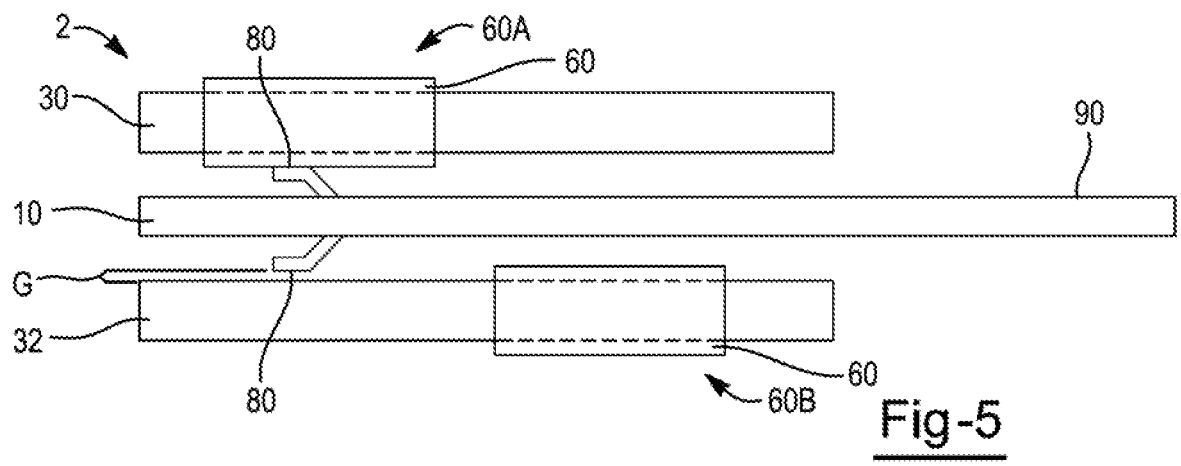
FIG. 5 illustrates a plan view of forceps including one shuttle in a first position and one shuttle in a second position.

FIG. 5 illustrates the forceps 2 with a first working arm 30 and a second working arm 32 with a body 10 located therebetween. A bias device 80 is located on a first side of the body 10 proximate to the first working arm 30 and a bias device 80 is located on a second side of the body 10 proximate to the second working arm 32. The body 10 is in communication with a blade 90 that is extended distal of the first working arm 30 and second working arm 32. The shuttle 60 on first working arm 30 is located in a first position 60A, and the shuttle 60 on the second working arm 32 is located in a second position 60B. A deactivation feature 14, which is a gap (G), is located between the second working arm 32 and the bias device 80 on the second side of the body 10 so that the bias device 80 is free of contact with the second working arm 32 and second working arm 32 is not biased. The shuttle 60 on the first working arm 30 fills the gap located between the first working arm 30 and the bias device 80 so that the first working arm 30 is biased by the bias device 80 contacting the shuttle 60 on the first working arm.

Figure 6:
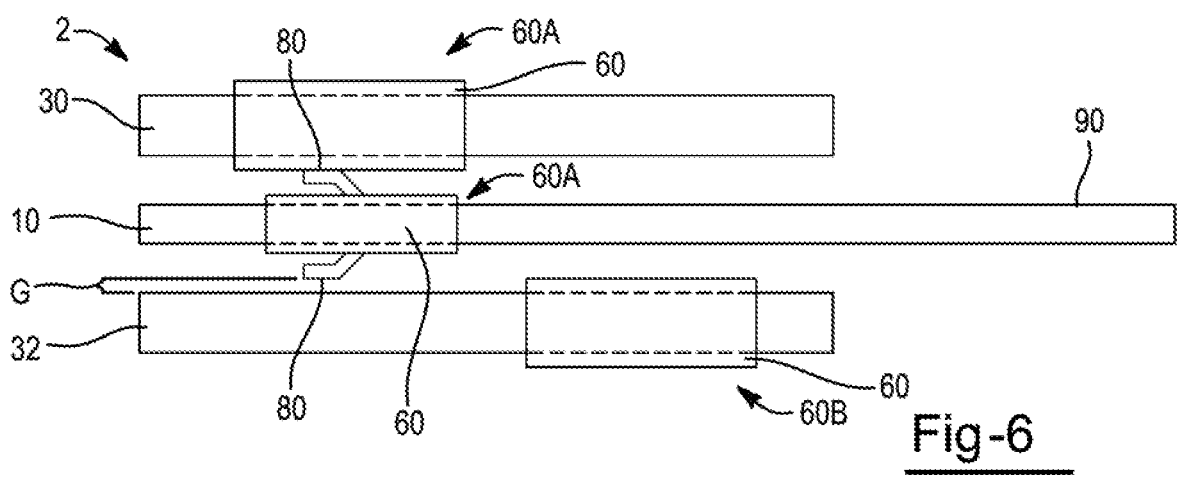
FIG. 6 illustrates a plan view of forceps including a shuttle on each working arm and one shuttle on the body.

FIG. 6 illustrates the forceps 2 with a first working arm 30 and a second working arm 32 with a body 10 located therebetween. A bias device 80 is located on a first side of the body 10 proximate to the first working arm 30 and a bias device 80 is located on a second side of the body 10 proximate to the second working arm 32. The shuttle 60 on first working arm 30 is located in a first position 60A (i.e., proximal position), and the shuttle 60 on the second working arm 32 is located in a second position 60B (i.e., distal position). A shuttle 60 is located on the body 10 and, as shown, the shuttle 60 is in a first position 60A. The blade 90 is extended distal of the first working arm 30 and the second working arm 32. The shuttle 60 on the first working arm 30 fills the gap located between the first working arm 30 and the bias device 80 so that the first working arm 30 is biased by the bias device 80 contacting the shuttle 60 on the first working arm 30. A gap (G) is located between the bias device 80 and the second working arm 32 so that the second working arm 32 is not biased.

Figure 7:
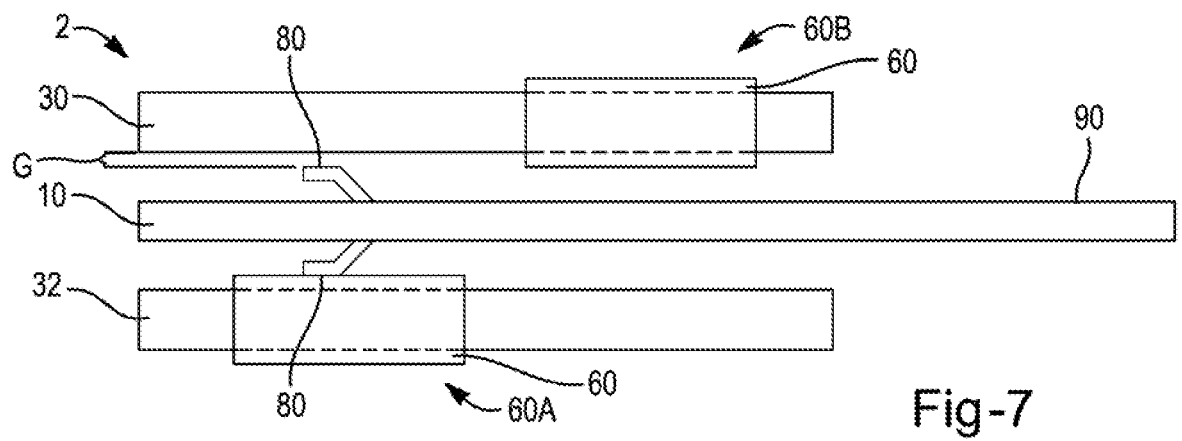
FIG. 7 illustrates a plan view of forceps with a shuttle on each working arm and a bias device on each side of a body.

FIG. 7 illustrates the forceps 2 with a first working arm 30 and a second working arm 32 with a body 10 located therebetween. A bias device 80 is located on a first side of the body 10 proximate to the first working arm 30 and a bias device 80 is located on a second side of the body 10 proximate to the second working arm 32. The body 10 is in communication with a blade 90 that, as shown, is extended distal of the first working arm 30 and the second working arm 32. The shuttle 60 on the first working arm 30 is in a second position 60B and the shuttle 60 on the second working arm 32 is in a first position 60A. A gap (G) is located between the shuttle 60 on the first working arm 30 and the bias device 80 on the first side of the body 10 and no gap is located between the second working arm 32 and the bias device 80 on the second side of the body 10 so only the second working arm 32 is biased and the first working arm 30 is free of bias.

Figure 8:
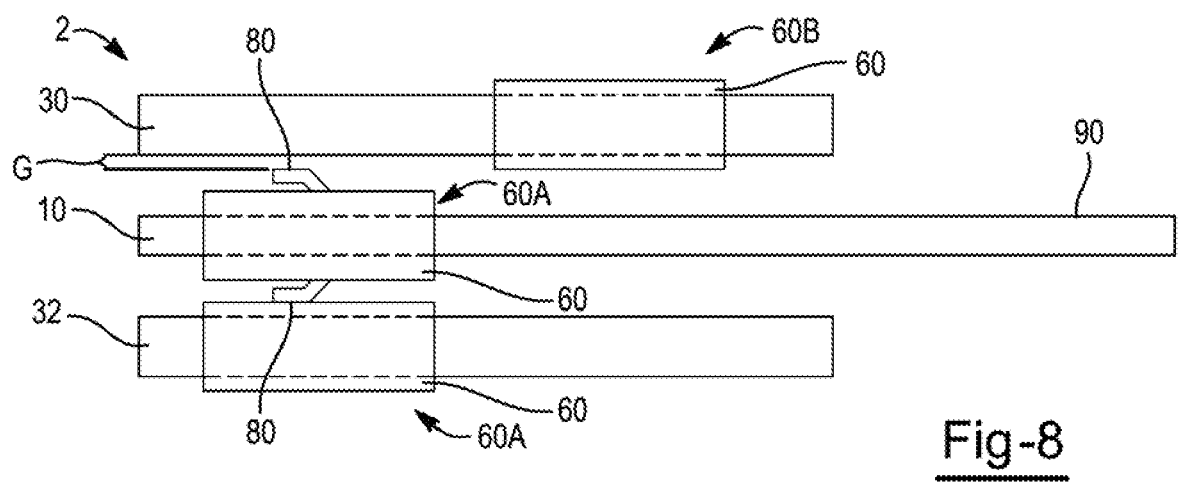
FIG. 8 illustrates a plan view of forceps including a shuttle on each working arm and one shuttle on the body with the shuttle on the second working arm being in a second position.

FIG. 8 illustrates the forceps 2 with a first working arm 30 and a second working arm 32 with a body 10 located therebetween. A shuttle 60 is movably connected to the body 10 and is shown in the first position 60A. A bias device 80 is located on a first side of the body 10 proximate to the first working arm 30 and a bias device 80 is located on a second side of the body 10 proximate to the second working arm 32. The body 10 is in communication with a blade 90 that is extended distal of the first working arm 30 and the second working arm 32. A shuttle 60 is located on the first working arm 30 in a second position 60B forming a gap (G) between the first working arm 30 and the bias device 80 so that the first working arm 30 is not biased. A shuttle 60 is located on the second working arm 32 in a first position 60A so that the bias device 80 on the shuttle 60 of the body 10 aligns with the shuttle 60 on the second working arm 32 and the bias device 80 biases the second working arm 32.

Figure 9:
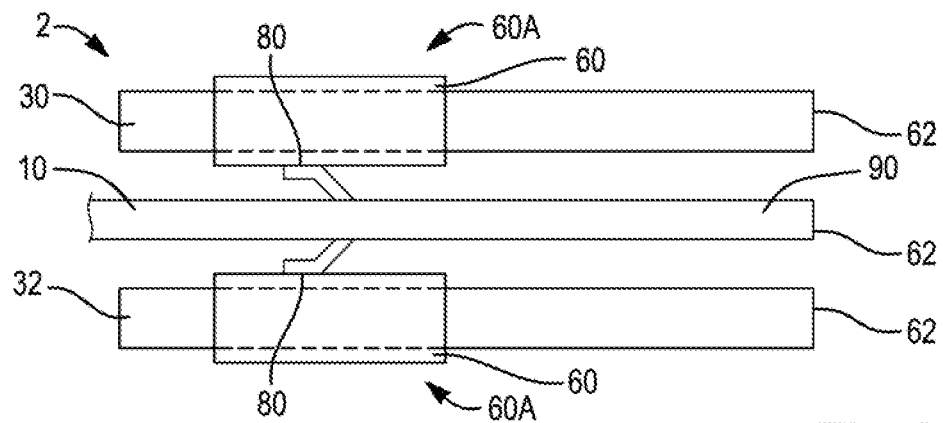
FIG. 9 illustrates forceps with a shuttle on each working arm and a blade being flush with a tip of each working arm.

FIG. 9 illustrates the forceps 2 with a first working arm 30 and a second working arm 32 with a body 10 located therebetween. A body 10 is in communication with a blade 90 and the blade 90 is retracted so that a distal end 62 of the blade is flush with the distal ends 62 of the first working arm 30 and the second working arm 32. A bias device 80 is connected to the body 10 and is located on a first side of the body 10 proximate to the first working arm 30 so that when the bias device 80 contacts the shuttle 60 on the first working arm 30, the first working arm 30 is biased. A bias device 80 is connected to the blade 90 and is located on a second side of the body 10 proximate to the second working arm 32 so that when the bias device 80 contacts the shuttle 60 on the second working arm 32, the second working arm 32 is biased. Both the shuttle 60 on the first working arm 30 and the shuttle 60 on the second working arm 32 are located in a first position 60A.

Figure 10A:
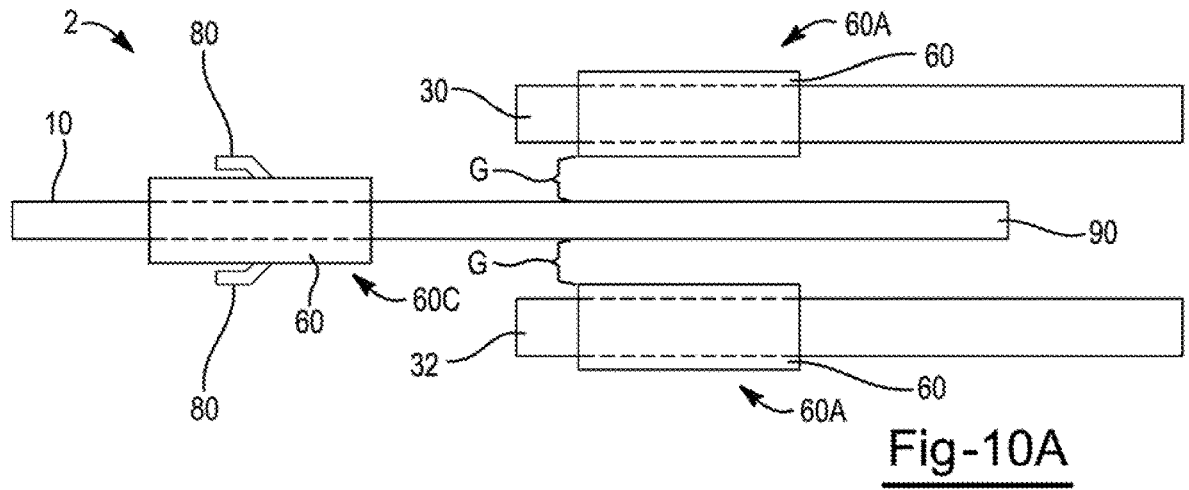
FIG. 10A illustrates forceps with a shuttle on each working arm in a first position and the blade being retracted along with a shuttle on the body.

FIG. 10A illustrates the forceps 2 with a first working arm 30 and a second working arm 32 with a body 10 located there between. The body 10 is in communication a blade 90 that is fully retracted allowing the first working arm 30 and the second working arm 32 full movement. The first working arm 30 includes a shuttle 60 in a first position 60A and the second working arm 32 includes a shuttle 60 in a first position 60A. A shuttle 60 is in communication with the body 10 and the blade 90. A bias device 80 is carried on the shuttle 60 on a first side proximate the first working arm 30 and on a second side proximate the second working arm 32. As shown, the shuttle 60 on the body 10 is in a third position 60C with blade fully retracted so that a gap (G) is located between the bias devices 80 and the first working arm 30 and second working arm 32 respectively.

Figure 10B:
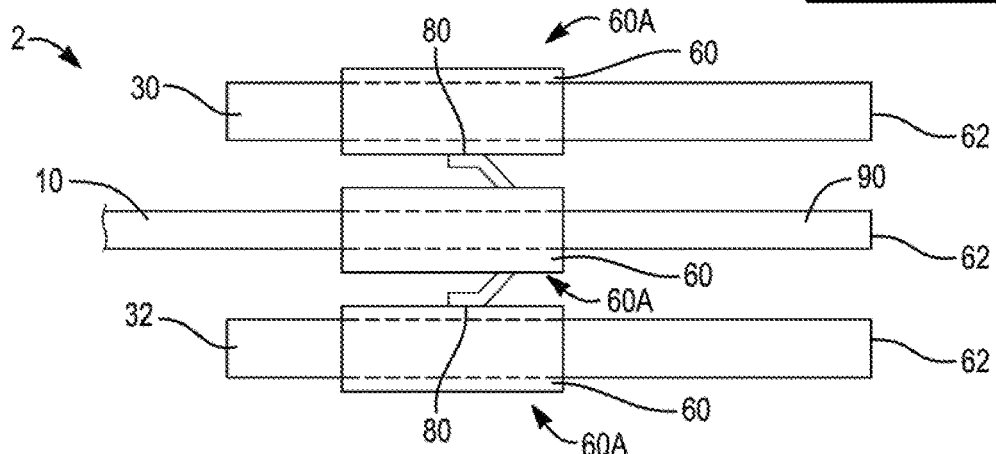
FIG. 10B illustrates a shuttle on each working arm in a first position and the blade being flush with a tip of each working arm and the shuttle on the body being in a first position and aligned with the shuttles on the working arms.

FIG. 10B illustrates the forceps 2 with a first working arm 30 and a second working arm 32 with a body 10 located therebetween. The body 10 is in communication with a blade 90 that has a distal end 62 that is flush with the distal ends 62 of the first working arm 30 and the second working arm 32. The first working arm 30 includes a shuttle 60 in a first position 60A and the second working arm 32 includes a shuttle in a first position 60A. A shuttle 60, carrying a bias device 80 on a first side and a bias device 80 on a second side, is located on the body 10 and the shuttle 60 is located in the first position 60A so that the bias devices 80 align with the shuttles 60 on the first working arm 30 and the second working arm 32 to bias the first working arm 30 and the second working arm 32 respectively.

Figure 10C:
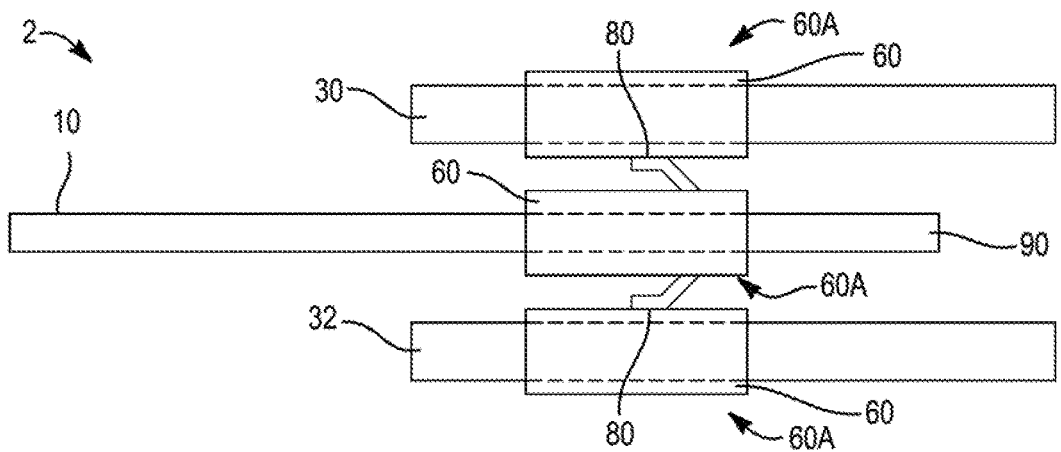
FIG. 10C illustrates forceps with a shuttle on each working arm in a first position and the blade being retracted, and a shuttle on the body being in a first position and opposing the shuttles on the working arms.

FIG. 10C illustrates the forceps 2 with a first working arm 30 and a second working arm 32 with a body 10 located therebetween. The body 10 is in communication a blade 90 that is fully retracted allowing the first working arm 30 and the second working arm 32 full movement. The first working arm 30 includes a shuttle 60 in a first position 60A and the second working arm 32 includes a shuttle in a first position 60A. A shuttle 60 is in communication with the body 10 and the blade 90. A bias device 80 is carried on the shuttle 60 on a first side proximate the first working arm 30 and on a second side proximate the second working arm 32. As shown, the shuttle 60 on the body 10 is in a first position 60A with blade fully retracted so that the bias devices 80 align with the shuttles 60 on the first working arm 30 and the second working arm 32 respectively to create a bias force.

Figure 10D:
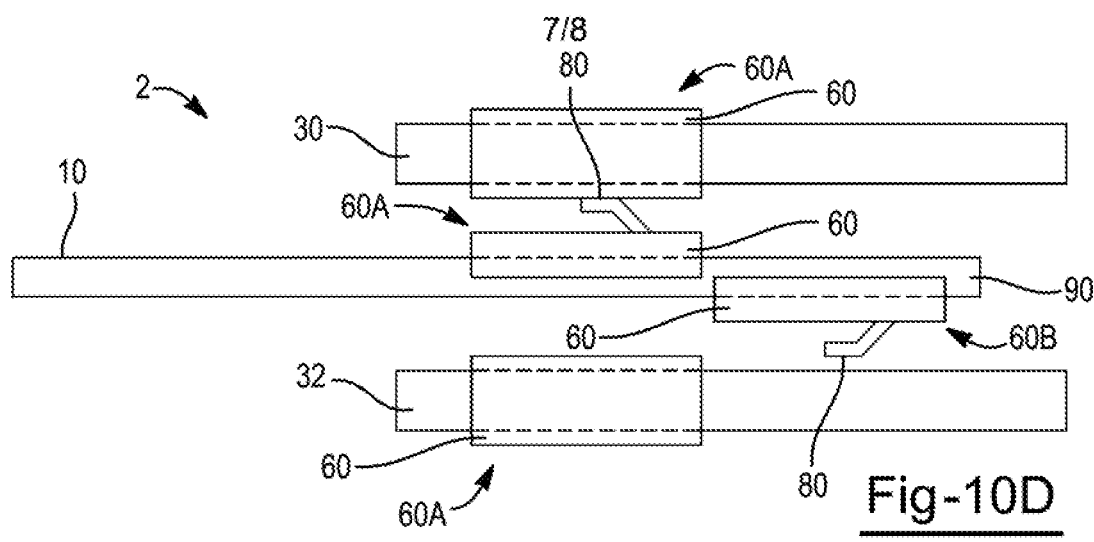
FIG. 10D illustrates a shuttle on each working arm and two shuttles on the body with one shuttle on the body being in a first position and one shuttle on the body being in a second position.

FIG. 10D illustrates the forceps 2 with a first working arm 30 and a second working arm 32 with a body 10 located therebetween. A shuttle 60 (e.g. a first shuttle portion) is located on the first working arm 30 in a first position 60A. A shuttle 60 (e.g., a third shuttle first portion) is located on the body 10 in a first position 60A so that a bias device 80 carried on the shuttle 60 is aligned with the shuttle 60 on the first working arm 30 so that the bias device 80 biases the first working arm 30. A shuttle 60 (e.g., a second shuttle portion) is located on the second working arm in a first position 60A. A second shuttle 60 (e.g., a third shuttle second portion) carrying a bias device 80 is located on the body 10 and/or blade 90 opposite the second working arm 32 and the second shuttle 60 is in a second position 60B so that a gap (G) is located between the bias device 80 and the shuttle 60 on the second working arm 32 so that the bias device 60 does not bias the second working arm 32.

Figure 11:
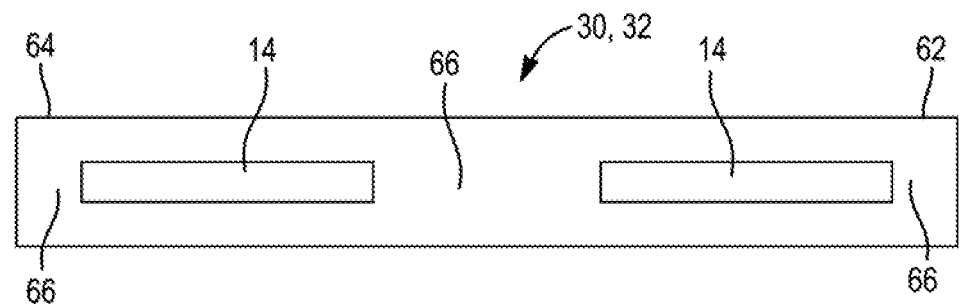
FIG. 11 is a plan view of a working arm including deactivation features and contact zones.

FIG. 11 illustrates a side view of the second working arm 32, the first working arm 30 being a mirror image of the second working arm 32. The working arms include a distal end 62 and a proximal end 64. As shown, there are a plurality of deactivation features 14. Between the deactivation features 14 are contact zones 66 where the bias members (not shown) can contact the first working arm 30 or second working arm 32 to bias the working arms.

Figure 12:
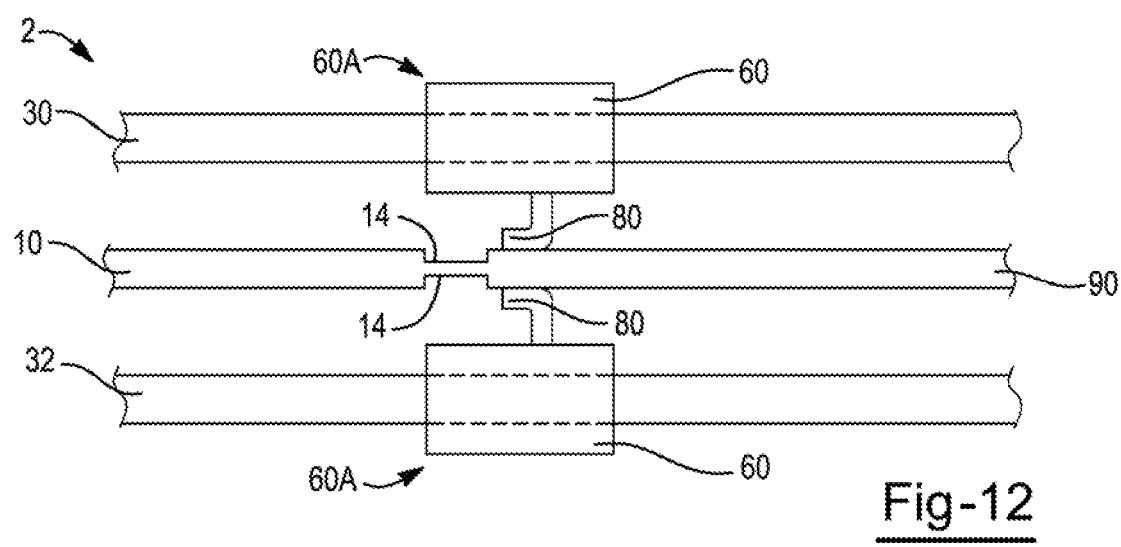
FIG. 12 illustrates a shuttle on each working arm with each working arm being biased.

FIG. 12 illustrates the forceps 2 with a first working arm 30 and a second working arm 32 with a body 10 located therebetween. The body 10 is connected to a blade 90 that extends from the body 10. The body 10 includes a deactivation feature 14 proximate to the first working arm 30 and a deactivation feature 14 proximate to the second working arm 32. The first working arm 30 includes a shuttle 60 with a bias device 80, the shuttle 60 being movable between a first position 60A and a second position (not shown). In the first position 60A, the shuttle 60 proximate to the first working arm 30 and the shuttle 60 proximate to the second working arm 32 align the bias devices 80 with the body 10 so that the first working arm 30 and the second working arm 32 bias against the body 10.

Figure 13:
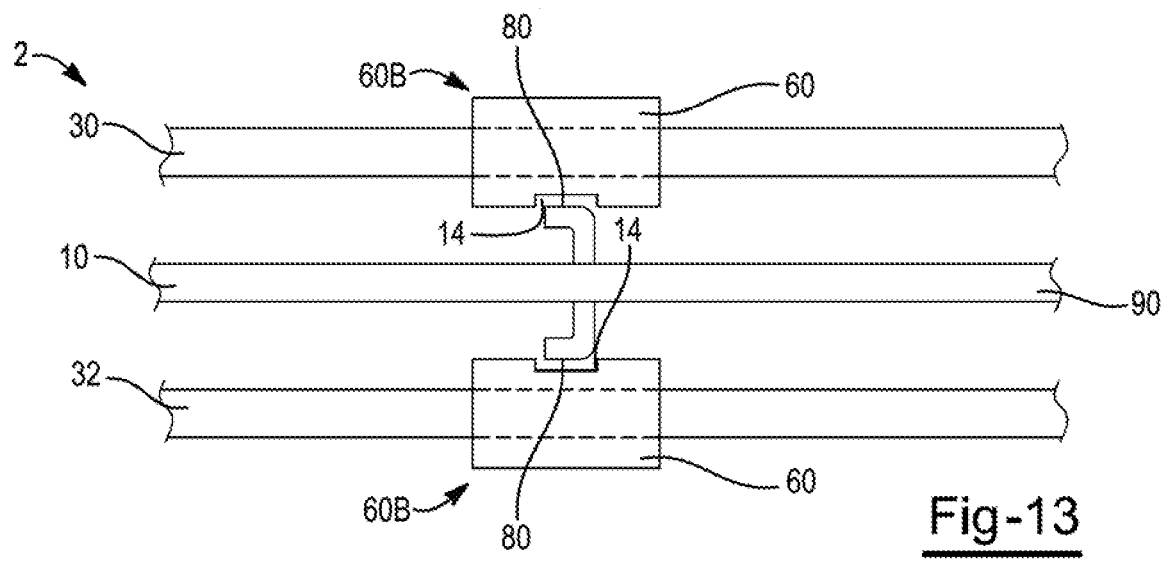
FIG. 13 illustrates both working arms being free of bias.

FIG. 13 illustrates the forceps 2 with a first working arm 30 and a second working arm 32 with a body 10 located therebetween. The body 10 is connected to a blade 90 that extends from the body 10. The body 10 includes a bias device 80 proximate to the first working arm 30 and a bias device 80 proximate to the second working arm 32. The first working arm 30 includes a shuttle 60 with a deactivation feature 14, the shuttle 60 moving between a first position (not shown) and a second position 60B. In the second position 60B, the shuttle 60 proximate to the first working arm 30 aligns the deactivation feature 14 with the bias member 80 so that the first working arm is not biased. The second working arm 32 includes a shuttle 60 with a deactivation feature 14, the shuttle moving between a first position (not shown) and a second position 60B. In the second position 60B, the shuttle 60 proximate to the second working arm 32 aligns the deactivation feature 14 with the bias device 80 proximate to the second working arm 32 so that the second working arm 32 is unable to bias against the bias device 80.

Figure 14:
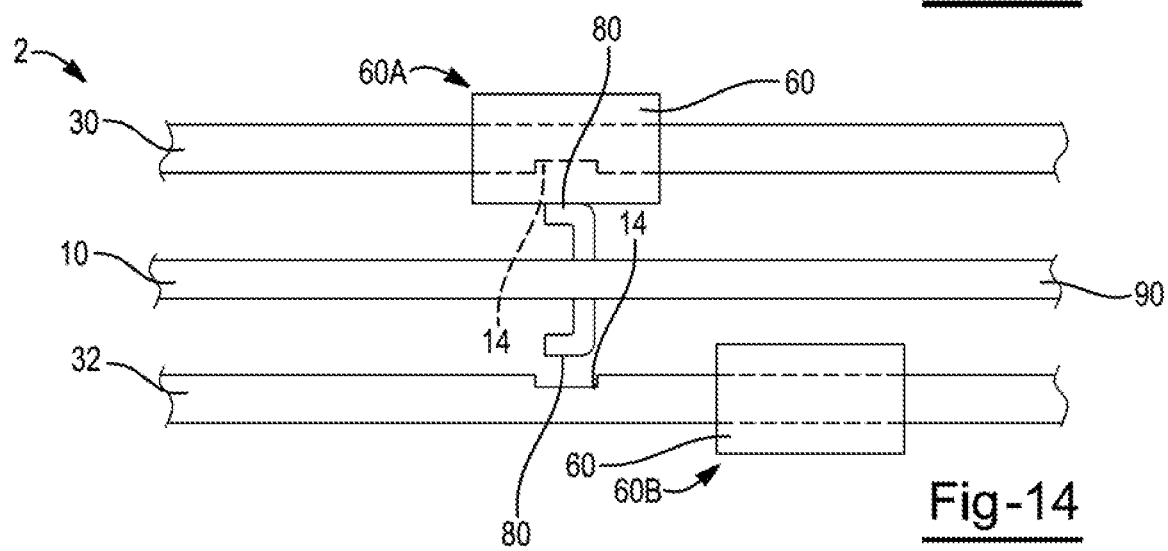
FIG. 14 illustrates one working arm being biased and one working arm being free of bias.

FIG. 14 illustrates the forceps 2 with a first working arm 30 and a second working arm 32 with a body 10 located therebetween. The body 10 includes a blade 90 extending therefrom. The body 10 includes a bias device 80 proximate to the first working arm 30 and a bias device 80 proximate to the second working arm 32. The first working arm 30 includes a deactivation feature 14 and a shuttle 60 which moves between a first position 60A and a second position (not shown). In the first position 60A, the shuttle 60 proximate to the first working arm 30 covers the deactivation feature 14 so the bias device 80 on the body 10 biases against the shuttle 60 on the first working arm 30. The second working arm 32 includes a deactivation feature 14 and a shuttle 60 which moves between a first position (not shown) and a second position 60B. In the second position 60B, the shuttle 60 proximate to the second working arm 32 uncovers the deactivation feature 14 so the bias device 80 is aligned with the deactivation feature 80 preventing the second working arm 32 or the shuttle 60 from biasing against the bias device 80 on the body 10.

Figure 15:
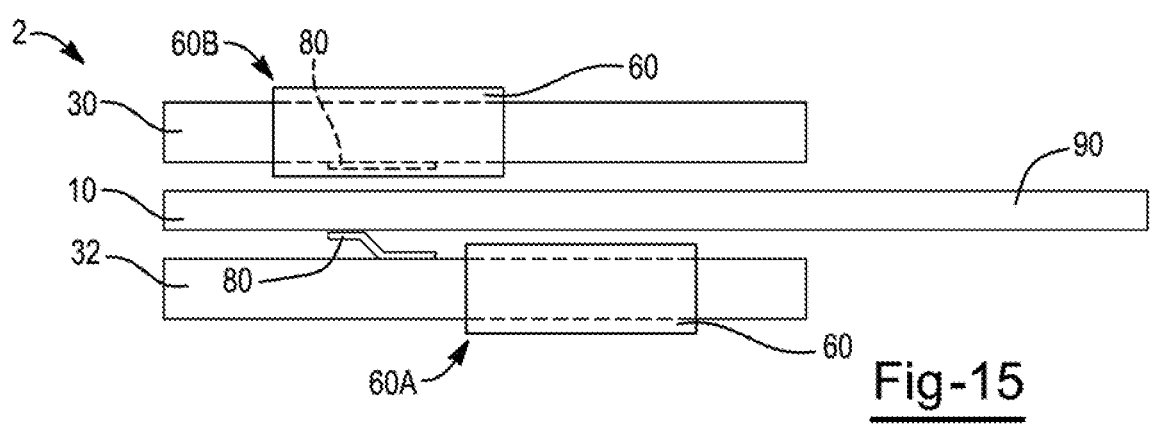
FIG. 15 illustrates a shuttle and bias device located on each working arm with the bias device being deactivated by the shuttle extending over and the bias device.

FIG. 15 illustrates the forceps 2 with a first working arm 30 and a second working arm 32 with a body 10 located therebetween. The body 10 includes a blade 90 extending therefrom. The first working arm 30 includes a bias device 80 and a shuttle 60 which moves between a first position (not shown) and a second position 60B. The shuttle 60 in the second position 60B slides over the bias device 80 so that the shuttle 60 compresses the bias device 80 and deactivates the bias device 80 so that the first working arm is free from biasing relative to the body 10. The second working arm 32 includes a bias device 80 and a shuttle 60 which moves between a first position 60A and a second position (not shown). The shuttle 60 in the first position 60A is not in contact with the bias device 80 so that the bias device 80 is in communication with the body 10 and the bias device 80 of the second working arm 32 biases against the body 10.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Forceps
10 Body
12 Inner shell
14 Deactivation feature
16 First activation button
18 Second activation button
20 Handle
30 First working arm
32 Second working arm
33 Electrode
34 Boss
36 Pivot pin
37 Pivot
38 Electrical path
40 Distal end
42 Cross Over
44 Gripping portion
60 Shuttle
60A First position
60B Second position
60C Third position
62 Distal end
64 Proximal end
66 Contact Zone
80 Bias device
82 Free end
84 Constrained end
86 Contact portion of spring
88 Breaks
90 Blade
100 Electrosurgical Device

We claim:

1. A device having a longitudinal axis comprising:
 a. a first working arm;
 b. a body;
 c. a shuttle movable between at least a first position and a second position along the longitudinal axis; and
 d. a bias device including a biasing surface;
 wherein the bias device biases the first working arm outward relative to the body when the shuttle is in the first position by physical contact between the biasing surface and the shuttle, the physical contact caused by movement of the shuttle from the second position to the first position along the longitudinal axis; and
 wherein the bias device is free of biasing the first working arm outward relative to the body when the shuttle is in the second position, the biasing surface of the bias device being free of physical contact with the shuttle in the second position.

2. The device of claim 1, wherein the device includes a second working arm.

3. The device of claim 1, wherein the bias device biases the first working arm away from the body when the shuttle is in the first position.

4. The device of claim 1, wherein the shuttle is located on the first working arm.

5. The device of claim 4, wherein the first working arm includes one or more deactivation features.

6. The device of claim 5, wherein the shuttle covers at least one of the one or more deactivation features when the shuttle is in the first position.

7. The device of claim 5, wherein at least one of the one or more deactivation features are exposed when the shuttle is in the second position.

8. The device of claim 7, wherein at least a portion of the bias device extends into the at least one of the one or more deactivation features that are exposed so that the first working arm is free of biasing when the shuttle is in the second position.

9. The device of claim 1, wherein the biasing surface of the bias device contacts the shuttle when the shuttle is in the first position.

10. The device of claim 1, wherein a gap is located between the bias device and the shuttle or the bias device and the first working arm when the shuttle is in the second position so that the bias device is prevented from biasing the first working arm.

11. The device of claim 1, wherein the device includes one or more deactivation features that are located in the shuttle.

12. The device of claim 11, wherein the shuttle covers at least one of the one or more deactivation features when the shuttle is in the first position, and at least one of the one or more deactivation features are exposed by the shuttle when the shuttle is in the second position.

13. The device of claim 1, further comprising a second working arm, wherein the shuttle is a first shuttle portion that is located on the first working arm and a second shuttle portion that is located on the second working arm.

14. The device of claim 13, wherein the bias device is located on the first shuttle portion, the second shuttle portion, the body, the first working arm, the second working arm, or a combination thereof.

15. The device of claim 13, wherein the first working arm, the second working arm, the body, the first shuttle portion, the second shuttle portion, or a combination thereof include one or more deactivation features.

16. The device of claim 13, wherein the first shuttle portion covers one or more deactivation features in the first working arm, misaligns one or more deactivation features in the first shuttle portion with the bias device, or misaligns one or more deactivation features in the body with the bias device when the first shuttle portion is in the first position; the second shuttle portion covers one or more deactivation features in the second working arm, misaligns one or more deactivation features in the second shuttle portion with the bias device, or misaligns one or more deactivation features in the body with the bias device when the second shuttle portion is in the first position; or both.

17. The device of claim 16, wherein the bias device extends into the one or more deactivation features when the first shuttle portion, the second shuttle portion, or both are located in the second position.

18. A device comprising:
 a. a first working arm;
 b. a second working arm;
 c. a body;
 d. a shuttle; and
 e. a bias device;
 wherein the bias device biases the first working arm relative to the body when the shuttle is in a first position,
 wherein the bias device is free of biasing the first working arm relative to the body when the shuttle is in a second position, and
 wherein the shuttle is located on the first working arm and the second working arm is free of a shuttle so that the first working arm is biased when the shuttle is in the first position and the second working arm is freely movable.

19. The device of claim 18, wherein the shuttle is longitudinally movable or rotationally movable.

20. A device comprising:
 a. a first working arm;
 b. a body;
 c. a shuttle located on the first working arm; and
 d. a bias device extending from the body and comprising an elastically deformable element;
 wherein the first working arm includes one or more deactivation features operable to deactivate the bias device;
 wherein the bias device biases the first working arm relative to the body when the shuttle is in a first position, the bias device in physical contact with the first working arm or the shuttle in the first position; and
 wherein the bias device is free of biasing the first working arm relative to the body when the shuttle is in a second position and the bias device is deactivated, the bias device being free of physical contact with the first working arm or the shuttle in the second position.

21. The device of claim 20, wherein when the shuttle is in the second position a gap is formed between the bias device and the first working arm or the bias device and the shuttle to prevent the bias device from biasing the first working arm.

* * * * *